US011628011B2

(12) United States Patent
Hodges et al.

(10) Patent No.: US 11,628,011 B2
(45) Date of Patent: *Apr. 18, 2023

(54) HEALTH IMAGING INFORMATICS SYSTEM AND METHODS

(71) Applicant: Synaptive Medical Inc., Toronto (CA)

(72) Inventors: Wesley Bryan Hodges, Toronto (CA); Norman Pyo, Toronto (CA); Cameron Anthony Piron, Toronto (CA); Kelly Noel Dyer, Toronto (CA)

(73) Assignee: Synaptive Medical Inc.

( * ) Notice: Subject to any disclaimer, the term of this patent is extended or adjusted under 35 U.S.C. 154(b) by 477 days.

This patent is subject to a terminal disclaimer.

(21) Appl. No.: 16/906,747

(22) Filed: Jun. 19, 2020

(65) Prior Publication Data

US 2020/0383730 A1 Dec. 10, 2020

Related U.S. Application Data

(63) Continuation of application No. 15/119,003, filed as application No. PCT/CA2014/050873 on Sep. 15, 2014, now Pat. No. 10,687,897.

(51) Int. Cl.
*A61B 34/10* (2016.01)
*G16H 50/70* (2018.01)
(Continued)

(52) U.S. Cl.
CPC ............ *A61B 34/10* (2016.02); *A61B 5/0075* (2013.01); *A61B 5/7246* (2013.01);
(Continued)

(58) Field of Classification Search
CPC ........ A61B 34/10; A61B 34/25; G16H 20/40; G16H 50/20
See application file for complete search history.

(56) References Cited

U.S. PATENT DOCUMENTS

| | | |
|---|---|---|
| 6,611,846 B1 | 8/2003 | Stoodley |
| 7,787,699 B2 | 8/2010 | Mahesh et al. |

(Continued)

FOREIGN PATENT DOCUMENTS

| | | |
|---|---|---|
| CN | 101477706 | 7/2009 |
| CN | 101515982 A | 8/2009 |

(Continued)

OTHER PUBLICATIONS

Miriam H. A. Bauer, et al., "Reconstruction of White Matter Tracts via Repeated Deterministic Streamline Tracking—Initial Experience", May 6, 2013, PLOS one, May 2013 vol. 8, Issue 5 e63082 (Year: 2013).*

(Continued)

*Primary Examiner* — Evangeline Barr

(57) ABSTRACT

Methods and systems for providing treatment planning information for a neurology procedure, including neurosurgical procedures. A database containing historical data about historical procedures is accessed. Historical data relevant to a neurology procedure is determined, based on a determination of similarity to a set of data characterizing the neurology procedure. Historical instances of procedure parameters relevant to the neurology procedure are determined and displayed.

20 Claims, 16 Drawing Sheets

(51) Int. Cl.

| | | |
|---|---|---|
| *G16H 50/20* | (2018.01) | |
| *G16H 10/40* | (2018.01) | |
| *G16H 20/40* | (2018.01) | |
| *G16H 40/20* | (2018.01) | |
| *G16H 30/20* | (2018.01) | |
| *G16H 10/60* | (2018.01) | |
| *G06T 7/30* | (2017.01) | |
| *A61B 34/00* | (2016.01) | |
| *A61B 17/34* | (2006.01) | |
| *A61B 5/00* | (2006.01) | |
| *G06T 7/00* | (2017.01) | |
| *G16H 50/50* | (2018.01) | |
| *G16H 30/40* | (2018.01) | |
| *A61B 34/20* | (2016.01) | |
| *A61B 90/50* | (2016.01) | |
| *A61B 90/57* | (2016.01) | |
| *A61B 90/00* | (2016.01) | |
| *G16H 70/20* | (2018.01) | |
| *A61B 90/10* | (2016.01) | |

(52) U.S. Cl.
CPC .......... *A61B 17/3421* (2013.01); *A61B 34/20* (2016.02); *A61B 34/25* (2016.02); *G06T 7/0014* (2013.01); *G06T 7/30* (2017.01); *G16H 10/40* (2018.01); *G16H 20/40* (2018.01); *G16H 30/20* (2018.01); *G16H 30/40* (2018.01); *G16H 40/20* (2018.01); *G16H 50/20* (2018.01); *G16H 50/50* (2018.01); *G16H 50/70* (2018.01); *A61B 90/50* (2016.02); *A61B 2034/101* (2016.02); *A61B 2034/105* (2016.02); *A61B 2034/107* (2016.02); *A61B 2034/2051* (2016.02); *A61B 2034/2055* (2016.02); *A61B 2034/252* (2016.02); *A61B 2034/256* (2016.02); *A61B 2090/103* (2016.02); *A61B 2090/365* (2016.02); *A61B 2090/374* (2016.02); *A61B 2090/378* (2016.02); *A61B 2090/3762* (2016.02); *A61B 2090/571* (2016.02); *A61B 2576/026* (2013.01); *G06T 2207/30016* (2013.01); *G16H 10/60* (2018.01); *G16H 70/20* (2018.01)

(56) References Cited

U.S. PATENT DOCUMENTS

| | | |
|---|---|---|
| 8,214,224 B2 | 7/2012 | Rao et al. |
| 9,589,104 B2 | 3/2017 | Heywood |
| 2005/0207531 A1 | 9/2005 | Dempsey et al. |
| 2006/0129140 A1 | 6/2006 | Todd et al. |
| 2007/0103459 A1 | 5/2007 | Stoval, III et al. |
| 2008/0235052 A1* | 9/2008 | Node-Langlois ...... G16H 50/50 705/2 |
| 2009/0089034 A1 | 4/2009 | Penny et al. |
| 2009/0118640 A1 | 5/2009 | Miller et al. |
| 2009/0326336 A1 | 12/2009 | Lemke et al. |
| 2010/0088117 A1 | 4/2010 | Belden et al. |
| 2012/0099778 A1 | 4/2012 | Helm et al. |
| 2012/0172705 A1* | 7/2012 | Jain .................. G01R 33/56341 600/410 |
| 2012/0197619 A1 | 8/2012 | Namer Yelin et al. |
| 2013/0030499 A1 | 1/2013 | Pouratian |
| 2013/0346109 A1 | 12/2013 | Gunn |
| 2014/0018677 A1 | 1/2014 | Sharonov |
| 2014/0081659 A1 | 3/2014 | Nawana et al. |
| 2014/0088990 A1 | 3/2014 | Nawana et al. |
| 2014/0108983 A1 | 4/2014 | William et al. |
| 2014/0148816 A1 | 5/2014 | McDonald et al. |
| 2014/0161338 A1 | 6/2014 | Machado |

FOREIGN PATENT DOCUMENTS

| | | |
|---|---|---|
| DE | 102004049258 B4 | 4/2007 |
| JP | 2007130461 A | 5/2007 |
| JP | 2008229332 A | 10/2008 |
| WO | 20130013690 A1 | 1/2013 |
| WO | 20140008613 A1 | 1/2014 |

OTHER PUBLICATIONS

Lauren J. O'Donnell and Carl-Fredrik Westin, "Automatic Tractography Segmentation Using a High-Dimensional White Matter Atlas", IEEE Transactions on Medical Imaging, vol. 26, No. 11, Nov. 2007 (Year: 2007).*

Extended European Search Report re: corresponding EP Application No. 14885103.3 dated Oct. 16, 2017.

Office Action re: corresponding CN Application No. 2014800770870 dated Jul. 9, 2018.

Search Report re: corresponding CN Application No. 201400770870 dated Jun. 29, 2018.

Office Action re: corresponding JP Application No. 2016-574308 dated Jun. 25, 2018.

Office Action re: corresponding AU Application No. 2014386694 dated Feb. 12, 2019.

Rizea Radu Eugen, MD; "New Application of Diffusion Tensor Imaging in neurosurgery"; Journal of Medicine and Life, vol. 4, Issue 4, Oct.-Dec. 2011, pp. 372-376 Sep. 9, 2011.

Richter M, Zolal A, Ganslandt O, Buchfelder M, Nimsky C, et al. "Evaluation of Diffusion-Tensor Imaging-Based Global Search and Tractography for Tumor Surgery Close to the Language System". PLoS One 8(1): e50132. doi:10.1371/journal.pone .0050132 2013.

* cited by examiner

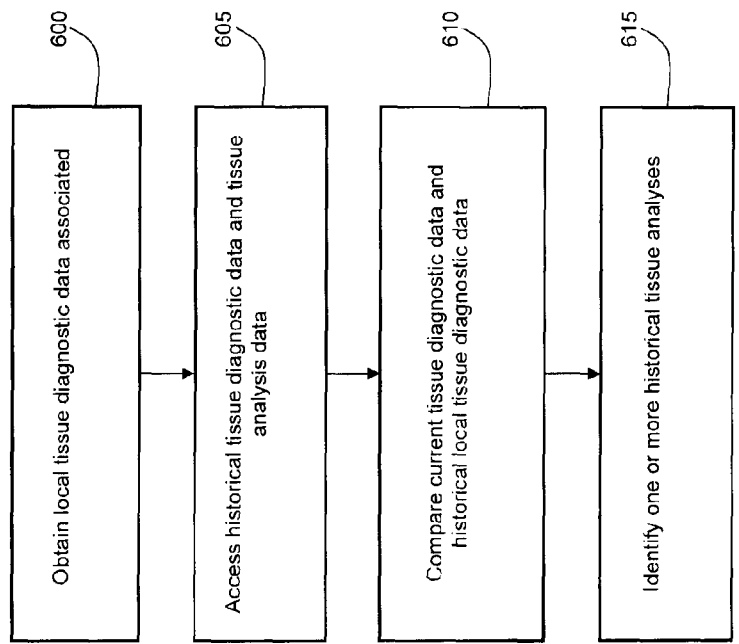

HEALTH IMAGING INFORMATICS SYSTEM AND METHODS

CROSS-REFERENCE TO RELATED APPLICATION(S)

This document is a continuation patent application claiming priority to, and the benefit of, U.S. patent application Ser. No. 15/119,003, entitled "SYSTEM AND METHOD FOR HEALTH IMAGING INFORMATICS," and filed on Aug. 15, 2016, claiming priority to, and the benefit of, PCT Application PCT/CA2014/050269, titled "INTRAMODAL SYNCHRONIZATION OF SURGICAL DATA," and filed on Mar. 14, 2014, all of which are hereby incorporated by reference in their entirety.

FIELD

The present disclosure relates to imaging methods for use in minimally invasive therapy, image guided medical procedures using multi-modal imaging modalities, and methods and systems for providing treatment planning information.

BACKGROUND

The term "informatics" has been used in various different contexts in medicine. In radiology, "informatics" may be used to refer to management of digital images, typically in the form of a picture archiving and communication system (PACS), and so the term "imaging informatics" may be more accurate. Systems for this type of management include Philips's IntelliSense™ PACS, Siemens's Syngo™ framework, and GE's Centricity™ PACS and Imaging Analytics products, among others, and the focus of these systems is generally limited to the storage, organization, and access of DICOM images.

In a surgical context, on the other hand, "informatics" has been used to refer to a broad and diverse range of operating room aspects. GE offers perioperative software that helps manage operating room (OR) scheduling, anesthesia documentation, surgical supplies, and throughput. NDS offers a series of products, e.g., ConductOR™, ScaleOR™, and ZeroWire™, focused on OR video streaming and distribution. Karl Storz's OR1 informatics platform is also centered on OR endoscopic video. Stryker offers iSuite™, which manages video, surgical lights, booms, and surgical navigation devices.

Other, more specialized, informatics systems exist in the cardiovascular space, consolidating various cardiac images, e.g., echocardiograms, X-rays, magnetic resonance (MR) images, etc., along with electrocardiogram (ECG) and electrophysiology results. The intent is to consolidate the plethora of data that comes from a variety of sources into a central place so that it is readily available to the clinician, e.g., the cardiologist, the cardiac surgeon, or another care provider, in its entirety, facilitating more informed decisions regarding a patient's care. Philips Xcelera™ and GE's Centricity™ Cardio are two commercially-available cardiovascular informatics systems.

As for other specialized surgical informatics platforms, Voyent Healthcare developed an orthopedic informatics solution over the mid to late 2000s. It features integrated orthopedic implant planning, web-based viewing, card swipe access, and operating room scheduling.

Contrary to the cardiovascular and orthopedic spaces, the specialized neurological/neurosurgical informatics landscape is sparse and underserved, despite the need and high demand among neurosurgeons for real-time information that can inform them on important clinical decisions before, during, and after surgery. This could be attributed to several key differences between the surgical disciplines, most notably the comparatively fewer imaging studies performed in neurosurgical procedures, which, in most cases, is limited to pre-operative MR or CT. However, with the growing demand and adoption of minimally invasive neurological procedures that require new sophisticated imaging tools for accurate guidance, this trend is quickly changing.

Thus, a need exists for integrating multi-modality imaging solutions that will take visualization, planning, and navigation, in pre-operative, intra-operative, and post-operative contexts to the next level to provide better care for patients.

SUMMARY

In various examples, the present disclosure provides systems and methods supporting the implementation of imaging and surgical informatics in neurology and neurosurgery.

In some examples, the present disclosure provides a computer implemented method for providing planning information for a neurology procedure, the method may include: receiving a first set of data characterizing the neurology procedure; accessing one or more historical databases containing historical data about historical procedures; determining one or more historical data relevant to the neurology procedure, based on a determination of similarity to the first set of data; determining, from the one or more historical data, one or more historical instances of one or more procedure parameters relevant to the neurology procedure; and displaying, on an output device, the one or more historical instances of the one or more procedure parameters.

In some examples, the present disclosure provides a computer implemented method for providing feedback for a neurology procedure, the method may include: accessing a remote database containing pre-procedure and post-procedure image data; determining, using identification information, a set of pre-procedure image data and a set of post-procedure image data associated with a given neurology procedure for a patient; performing a quantitative comparison of the pre-procedure image data and the post-procedure image data; and displaying, on an output device, the quantitative comparison.

In some examples, the present disclosure provides a system for providing information about a neurology procedure, the system may include: a central system, comprising one or more processors, in communication with two or more databases, each of the two or more databases storing different information associated with the neurology procedure; one or more data processing modules executable by the central system, the one or more data processing modules including at least one planning module that, when executed, causes the system to: receive a first set of data characterizing the neurology procedure; access one or more historical databases containing historical data about historical procedures; determine one or more historical data relevant to the neurology procedure, based on a determination of similarity to the first set of data; determine, from the one or more historical data, one or more historical instances of one or more procedure parameters relevant to the neurology procedure; and cause an output device to display the one or more historical instances of the one or more procedure parameters.

In some examples, the present disclosure provides a system for providing feedback about a neurology procedure, the system may include: a central system, comprising one or more processors, in communication with one or more remote databases containing pre-procedure and post-procedure image data; and one or more data processing modules executable by the central system, the one or more data processing modules including at least one feedback module that, when executed, causes the system to: access at least one remote database containing the pre-procedure and post-procedure image data; determine, using identification information, a set of pre-procedure image data and a set of post-procedure image data associated with a given neurology procedure for a patient; perform a quantitative comparison of the pre-procedure image data and the post-procedure image data; and cause an output device to display the quantitative comparison.

BRIEF DESCRIPTION OF THE DRAWINGS

Embodiments will now be described, by way of example only, with reference to the Drawings as follows:

FIG. 6 is a flowchart illustrating an example method of identifying similar prior tissue analyses by performing a similarity analysis between local diagnostic data and archival local tissue diagnostic data stored in a tissue analysis database;

DETAILED DESCRIPTION

Figure 1:
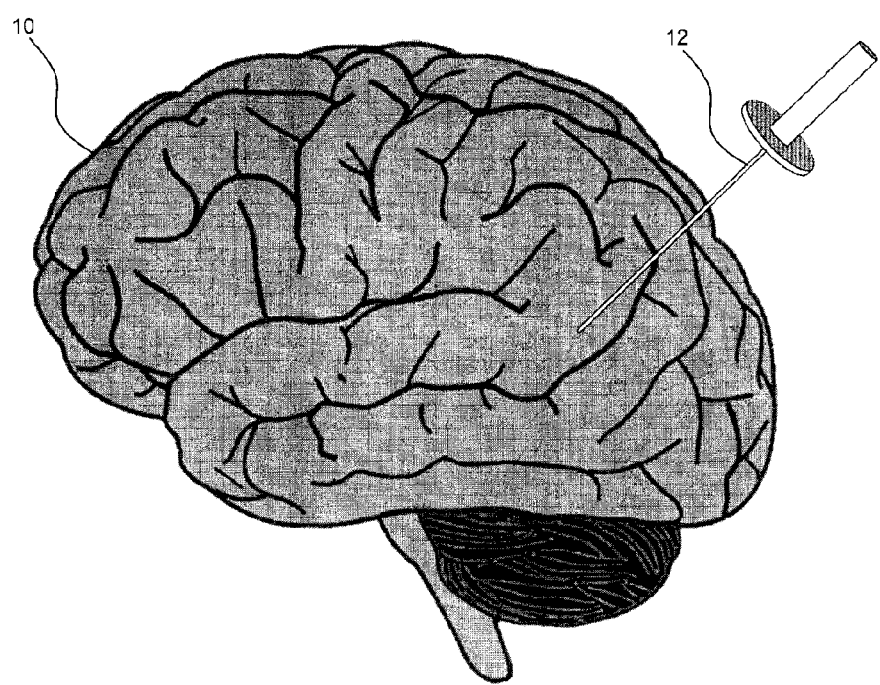
FIG. 1 is a diagram illustrating the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intra-operative" refers to an action, process, method, event or step that occurs or is carried out during at least a portion of a medical procedure. Intra-operative, as defined herein, is not limited to surgical procedures, and may refer to other types of medical procedures, such as diagnostic and therapeutic procedures.

It is noted that the phrase "outcome", as used herein, refers to quantifiable methods to measure mortality and morbidity of the subject. This includes, but is not limited to, measurement of actual patient function, including direct measures of tissue viability, or higher-level function, as well as in-direct measurements, tests and observations. An outcome may also refer to the economic outcome of a procedure (in a specific or broad sense), and may include the time for the procedure, the equipment and personal utilization, drug and disposable utilization, length of stay, and indications of complications and/or comorbidities.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures, e.g. minimally invasive medical procedures, are performed based on access to internal tissue through the access port.

In some examples, the present disclosure may provide an alternative to or a complementary system to conventional tissue sampling techniques. In many medical procedures, tissue samples are excised or examined, for example, during the surgical removal of a tumor. Conventionally, in the fields of medical imaging and surgical diagnostics, taking a tissue sample and performing histopathology examination of it using a microscope, often with staining of that tissue, remains the gold standard for tissue diagnosis. This typically involves resection in a surgical suite and transfer of the sample to a pathology laboratory. However, this approach may be fraught with problems and issues. For example, conventional methods of tissue analysis are typically unable to accurately and painlessly access tissue, and may possibly seed tumor cells through the biopsy process. It may also be impractical to perform multiple biopsies to enable proper examination of heterogeneous tumors. Tissue samples are also often mislabeled during the process, which can result due to sample mix-up or labeling errors, resulting in faulty diagnosis. Furthermore, pathology results may be discordant with the imaging results. Conventional workflow also often may have a poor feedback loop to radiologists, which may hinder them from improving their diagnostic accuracy for future cases. This also can result in an unnecessary delay between biopsy and pathology results, resulting in a reduction in positive patient outcomes.

In some examples, the present disclosure may enable the use of imaging and image guidance, to replace or supplement tissue sampling, for example as part of a multi-faceted treatment approach. In some examples, the present disclosure may help to integrate information from separate health systems and/or help to communicate information across separate health systems, such as health-care management systems from separate countries.

The health-care industries throughout the world typically consist of various systems of health-care management and treatment, from private health-care services to public, state-based and nationalized health-care systems to a combination of these systems at regional levels. Conventionally, it has been a challenge to integrate health systems from different countries. The variety of service structures available to patients across the United States of America (US) and Canada, for example, leads to several different methods of collection of health-related data, which may affect the availability of such data to researchers and administrative officials.

For example, in the US, the combination of data-management systems, laws around confidentiality and access with respect to patient-related health data may lead to difficulty in using data collected from patients to facilitate relevant and crucial research projects, and to develop policies and procedures for effective and innovative population-based health issues.

In another example, Canada's public patient health-record management systems are typically designed with two goals in mind: to provide researchers with relevant patient data for medical research purposes, and to aid administrators in the development of effective population-based health policies. Both of these aims may facilitate the progress of an integrated, interactive and intuitive health-care system that is built on the efficient allocation of research and policy resources. A public system of health-records collection and management may provide advantages, such as an understanding of surgical waiting lists, the utilization of resources by those with a specific health problem, and understanding the relationship between drug utilization and patient use of other health interventions.

Further, the data collected in public health care systems can be used to develop health-care management policies for populations, trace health-trends in populations and to address issues of ethics, confidentiality and long-term health of individuals and populations. Using the method of individual data sets to infer health trends for populations may be an important factor in effective health resource management.

Jurisdictions with nationalized health-care systems typically have methods in place to systematically collect and store patient information at the national, regional and provincial levels. However, the lack of aggregate data collection systems in the health-care field is problematic for jurisdictions without public health care, such as the US In the US, such a central data-collection and management system does not exist due to the lack of a centralized health-care system, the existence of private health-care providers, state-level health-care management policies that do not provide reciprocity in exchanging of patient information and health records and the existence of privacy laws that prevent the collection of health-related data for the purposes of the creation of population-based healthcare policies or institutional-based healthcare policies. The present disclosure may provide a way for centralizing and/or integrating such disparate sources of information.

In Canada, the current linked health data collection, storage and management systems divide patient information into six types of files which are arranged according to the information collected on individual patients through the health care system. These six types are: medical services, hospital separations, drug prescriptions for the elderly, long term care services, deaths and births. The current system is currently undergoing linkage based on a methodology that focuses on developing an aggregate system of data collection. One problem with this system is the existence of "grey areas" in the links, which lead to the possibility of false positives and bad links being developed, potentially misleading research trends, obfuscating methodologies and creating skewed results. Another problem with the current system is that it does not allow for data exchange across different systems, as would be the case if the Canadian health care data management systems were to be applied to the mix of public-private systems in the U.S., in their current state.

In some examples, embodiments of the present disclosure may enable better sharing of information across separate data sources within a given health system, as well as across separate health systems. Example embodiments of the present disclosure will be described with reference to neurology and neurosurgery procedures, as illustrated by the figures described below.

Referring to FIG. 1, this diagram illustrates the insertion of an access port into a human brain, for providing access to internal brain tissue during a medical procedure, in accordance with an embodiment of the present disclosure. An access port 12 is inserted into a human brain 10, providing access to internal brain tissue. The access port 12 may include such instruments as catheters, surgical probes, or cylindrical ports such as the NICO BrainPath™. Surgical tools and instruments may then be inserted within the lumen of the access port 12 in order to perform surgical, diagnostic or therapeutic procedures, such as resecting tumors as necessary. In some examples, the present disclosure may apply equally well to catheters, DBS needles, a biopsy procedure, and also to biopsies and/or catheters in other medical procedures performed on other parts of the body. In the example of a port-based surgery, a straight or linear access port 12 is typically guided down a sulci path of the brain 10. Surgical instruments would then be inserted down the access port 12.

Still referring to FIG. 1, optical tracking systems, used in the medical procedure, may track the position of a part of the instrument that is within line-of-site of the optical tracking camera. These optical tracking systems also typically require a reference to the patient to know where the instrument is relative to the target, e.g., a tumor, of the medical procedure. These optical tracking systems typically require a knowledge of the dimensions of the instrument being tracked so that, for example, the optical tracking system is able to determine the position in space of a tip of a medical instrument relative to the tracking markers being tracked.

Figure 2:
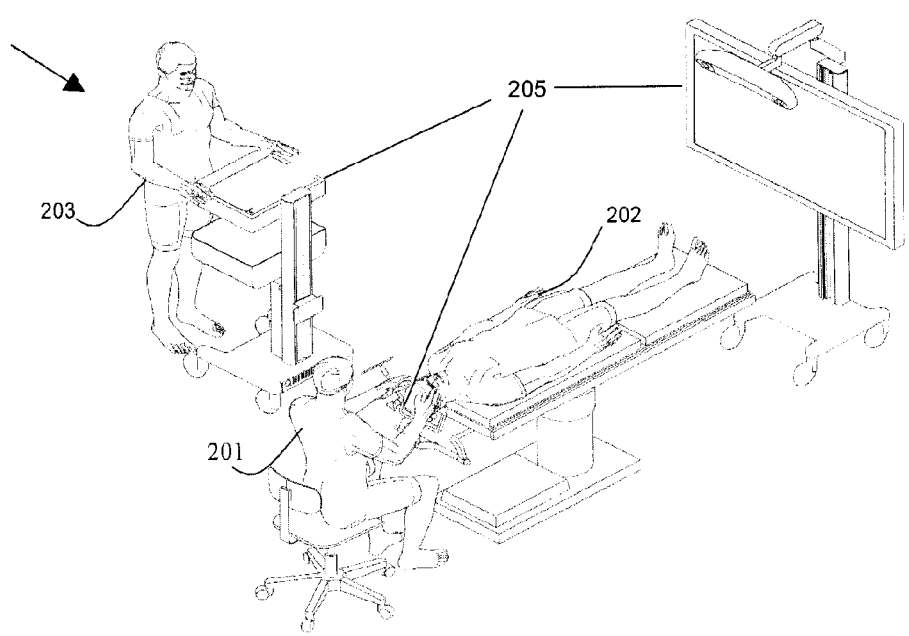
FIG. 2 is a diagram illustrating an exemplary navigation system to support minimally invasive access port-based surgery.

Referring to FIG. 2, this diagram illustrates an exemplary navigation system environment 200 is shown, which may be used to support navigated image-guided surgery, in accordance with an embodiment of the present disclosure. A surgeon 201 conducts a surgery on a patient 202 in an operating room (OR) environment. An example medical navigation system 205 comprising an equipment tower, tracking system, display(s) and tracked instrument(s) assist the surgeon 201 during his procedure. An operator 203 may also be present to operate, control and provide assistance for the medical navigation system 205.

Figure 3:
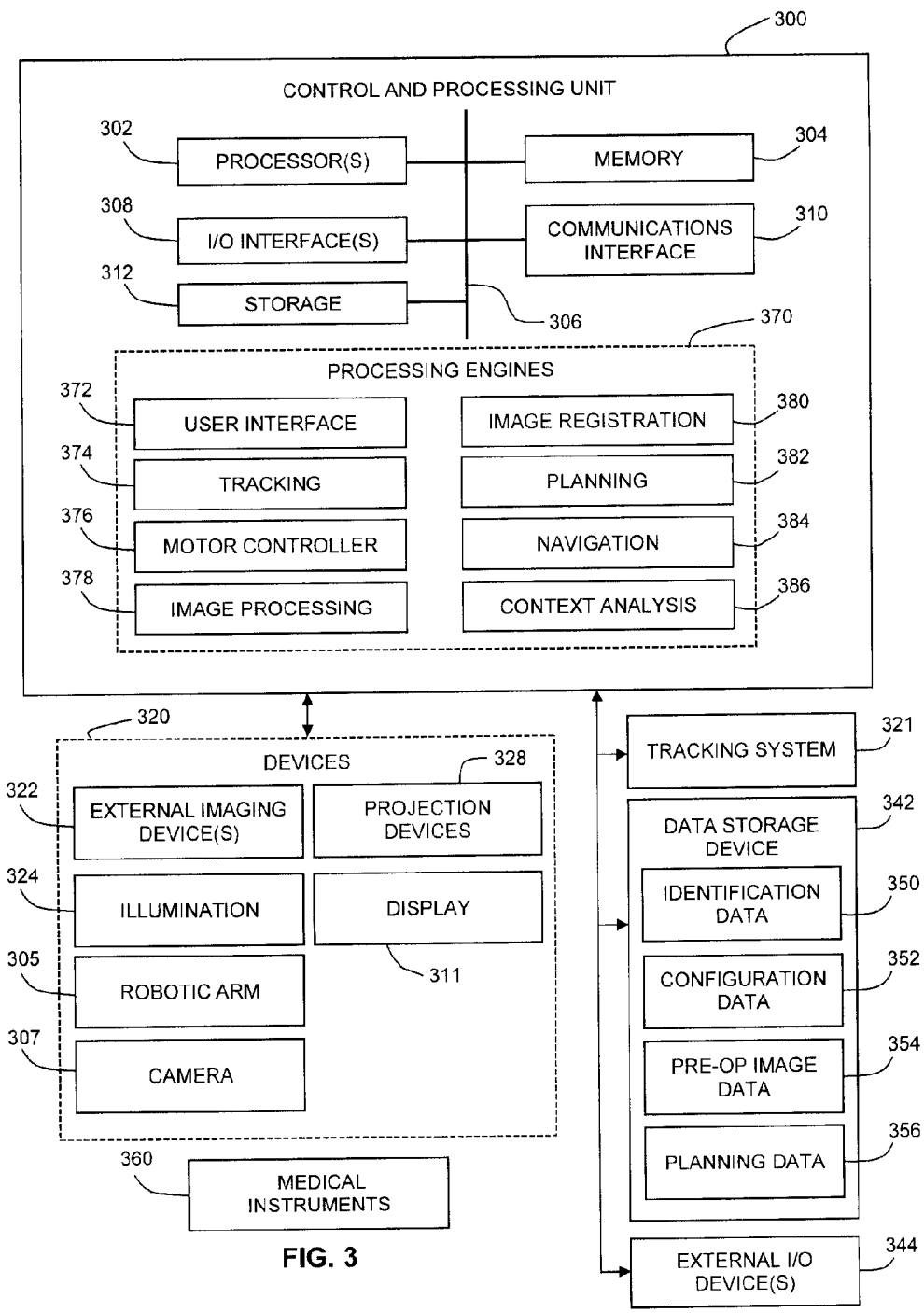
FIG. 3 is a block diagram illustrating a control and processing system that may be used in the navigation system shown in FIG. 2.

Referring to FIG. 3, this block diagram illustrates an example control and processing system 300 that may be used in the medical navigation system 205, as shown in FIG. 2, e.g., as part of the equipment tower, in accordance with an embodiment of the present disclosure. In one example, control and processing system 300 may include one or more processors 302, an internal and/or external memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device, e.g. a computer, hard drive, digital media device, or server, having a database stored thereon. The data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device, understood is that, in other embodiments, the data storage device 342 comprises multiple storage devices.

Still referring to FIG. 3, medical instruments 360 may be identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intra-operative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300.

Still referring to FIG. 3, control and processing unit 300 may also interface with a number of configurable devices, and may intra-operatively reconfigure one or more of such devices based on configuration parameters obtained from configuration data 352. Examples of devices 320 include one or more external imaging devices 322, one or more illumination devices 324, a robotic arm, the tracking camera 307, one or more projection devices 328, and one or more displays 311. Exemplary aspects of the disclosure are implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately, in one example the processing modules 370 are stored in the memory 304 and the processing modules may be collectively referred to as processing modules 370.

Still referring to FIG. 3, in some examples, the control and processing system 300 may include one or more interfaces, such as communications interface 310, for communicating with a central informatics system, as described further below. One or more processing modules or engines 370, such as the procedure planning engine 382 and the user interface engine 372, may receive data communicated from the informatics system and may use such data in its processing prior to, during, or after an operation, for example. The control and processing system 300 may also communicate data, such as image data from image processing engine 378, to the informatics system. Understood is that the control and processing system 300 is not intended to be limited to the components shown. For example, one or more components of the control and processing system 300 may be provided as an external component or device. In one example, navigation module 384 may be provided as an external navigation system that is integrated with control and processing system 300.

Still referring to FIG. 3, some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software. While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system, such as the control and processing system 300 described above, or other computer system, or other data processing system in response to its processor, such as a microprocessor, executing sequences of instructions contained in a memory, such as ROM, volatile RAM, non-volatile memory, cache or a remote storage device.

Still referring to FIG. 3, a computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices. Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc. At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Still referring to FIG. 3, according to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
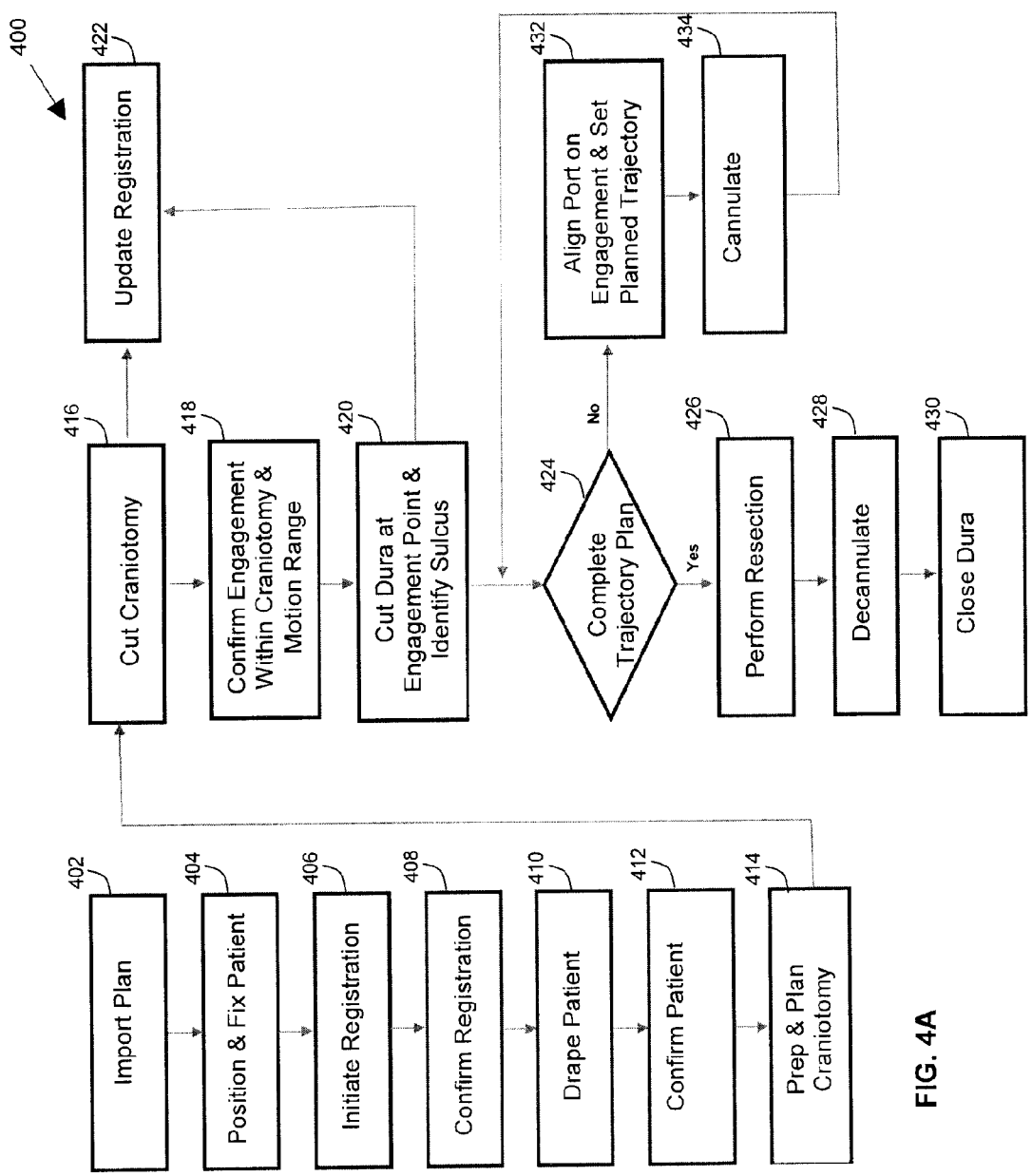
FIG. 4A is a flowchart illustrating a method involved in a surgical procedure using the navigation system of FIG. 2.

Referring to FIG. 4A, this flowchart illustrates an example method 400 of performing a port-based surgical procedure using a navigation system, such as the medical navigation system 205, as shown in FIG. 2, in accordance with an embodiment of the present disclosure. At a first block 402, the port-based surgical plan is imported. An example of the process to create and select a surgical plan is outlined in the disclosure "PLANNING, NAVIGATION AND SIMULATION SYSTEMS AND METHODS FOR MINIMALLY INVASIVE THERAPY", a United States Patent Publication based on a United States patent application, which claims priority to U.S. Provisional Patent Application Ser. Nos. 61/800,155 and 61/924,993, which are all hereby incorporated by reference in their entireties. Once the plan has been imported into the navigation system at the block 402, the patient is affixed into position using a body holding mechanism. The head position is also confirmed with the patient plan in the navigation system (block 404), which in one example may be implemented by the computer or controller forming part of the navigation system 205.

Still referring to FIG. 4A, next, registration of the patient is initiated (block 406). The phrase "registration" or "image registration" refers to the process of transforming different sets of data into one common coordinate system. Data may include multiple images, e.g., still photographs or videos, data from different sensors, times, depths, or viewpoints. The process of "registration" is used in the present application to refer to medical imaging in which images from different imaging modalities are co-registered. The navigation system may define a three-dimensional virtual space within which images may be registered, as described further below. Registration may be used in order to be able to compare or integrate the data obtained from these different modalities, for example. Other registration techniques are suitable and one or more of such techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods typically are used to register images acquired by different scanner or sensor types, for example in magnetic resonance imaging (MRI) and positron emission tomography (PET). In the present disclosure, multi-modality registration methods are used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
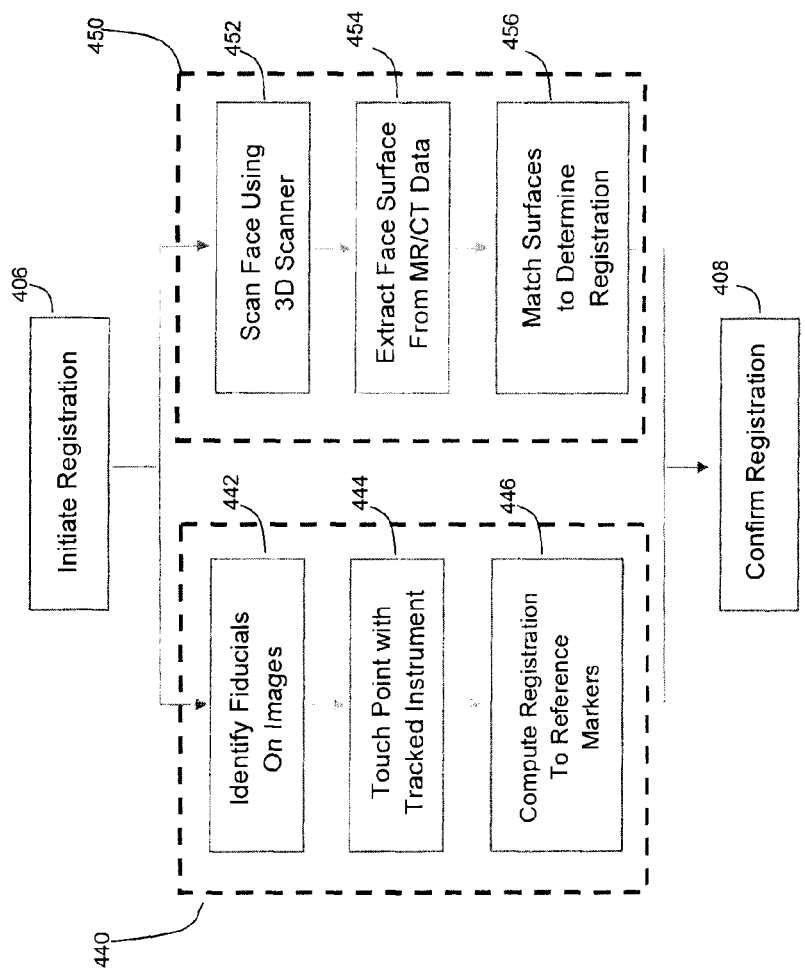
FIG. 4B is a flowchart illustrating a method of registering a patient for a surgical procedure, as shown in FIG. 4A.

Referring now to FIG. 4B and referring back to FIG. 4A, this flowchart illustrates a method involved in registration block 406, as shown in FIG. 4A, in greater detail, in accordance with an embodiment of the present disclosure. Block 440 illustrates an approach using fiducial touch points, while block 450 illustrates an approach using a surface scan. The block 450 is not typically used when fiducial touch points or a fiducial pointer is used. If the use of fiducial touch points (block 440) is contemplated, then the method may involve first identifying fiducials on images (block 442), then touching the touch points with a tracked instrument (block 444). Next, the navigation system computes the registration to reference markers (block 446).

Alternately, registration can be completed by conducting a surface scan procedure (block 450). In this approach, the patient's head. e.g., face, back of head and/or skull, is scanned using a 3D scanner (block 452). Next, the corresponding surface of the patient's head is extracted from pre-operative image data, such as MR or CT data (block 454). Finally, the scanned surface and the extracted surface are matched to each other to determine registration data points (block 456). Upon completion of either the fiducial touch points (440) or surface scan (450) procedures, the data extracted is computed and used to confirm registration at block 408. Once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms, e.g., bacteria, between non-sterile and sterile areas.

At this point, conventional navigation systems typically require that the non-sterile patient reference is replaced with a sterile patient reference of identical geometry location and orientation. Numerous mechanical methods may be used to minimize the displacement of the new sterile patient reference relative to the non-sterile one that was used for registration but it is expected that some error will exist. This error directly translates into registration error between the surgical field and pre-surgical images. In fact, the further away points of interest are from the patient reference, the worse the error will be.

Referring back to FIGS. 4A and 4B, upon completion of draping (block 410), the patient engagement points are confirmed (block 412) and then the craniotomy is prepared and planned (block 414). Planning the procedure may involve retrieving an existing partially-prepared treatment plan that may have been prepared based on the patient's pre-operative data. In some examples, a fully-prepared treatment plan may be retrieved, such as a previously performed treatment plan Planning the procedure is aided by information from the informatics system, described further below. Intra-operative data, such as the registered image of the patient's actual skull surface, may be used to adjust an existing partially-prepared treatment plan, for example. For safety and quality reasons, a surgeon may not rely completely on an automatically generated treatment plan, but such a plan may be used as a tool to assist the surgeon in planning the treatment.

Still referring back to FIGS. 4A and 4B, upon completion of the preparation and planning of the craniotomy, the craniotomy is cut and a bone flap is temporarily removed from the skull to access the brain (block 416). In some examples, cutting the craniotomy may be assisted by a visual indication of the location, size and/or shape of the planned craniotomy, e.g., a projection of a planned outline onto the patient's skull. Registration data may be updated with the navigation system at this point (block 422), as appropriate. Next, the engagement within craniotomy and the motion range are confirmed (block 418). Next, the procedure advances to cutting the dura at the engagement points and identifying the sulcus (block 420). Registration data may again be updated with the navigation system at this point (block 422). In some examples, by focusing the camera's view on the surgical area of interest, update of the registration data (block 422) may be adjusted to help achieve a better match for the region of interest, while ignoring any non-uniform tissue deformation, for example, affecting areas outside of the region of interest. Additionally, by matching image overlay representations of tissue with an actual view of the tissue of interest, the particular tissue representation may be matched to the live video image, which may help to improve registration of the tissue of interest. For example, the registration may enable: matching a live video of the post craniotomy brain (with the brain exposed) with an imaged sulcal map; matching the position of exposed vessels in a live video with image segmentation of vessels; matching the position of lesion or tumor in a live video with image segmentation of the lesion and/or tumor; and/or matching a video image from endoscopy up the nasal cavity with bone rendering of bone surface on nasal cavity for endonasal alignment. In some examples, multiple cameras can be used and overlaid with tracked instrument(s) views, which may allow multiple views of the image data and overlays to be presented at the same time. This may help to provide greater confidence in registration, or may enable easier detection of registration errors and their subsequent correction.

Still referring back to FIGS. 4A and 4B, in thereafter, the cannulation process is initiated. Cannulation typically involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424). In some examples, the cannulation process may also support multi-point trajectories where a target, e.g., a tumor, may be accessed by cannulating to intermediate points, then adjusting the cannulation angle to get to the next point in a planned trajectory. This multi-point trajectory may be contrasted with straight-line trajectories where the target may be accessed by cannulating along a straight path directly towards the target. The multi-point trajectory may allow a cannulation trajectory to skirt around tissue that the surgeon may want to preserve. Navigating multi-point trajectories may be accomplished by physically reorienting, e.g., adjusting the angle of, a straight access port at different points along a planned path, or by using a flexible port, such as an access port with manipulatable bends that may be bent along the multi-point trajectory. Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of embodiments, shown in FIGS. 4A and 4B, may be specific to port-based surgery, such as portions of blocks 428, 420, and 434, but the appropriate portions of these blocks may be skipped or suitably modified when performing non-port-based surgery.

Still referring back to FIGS. 4A and 4B, when performing a surgical procedure using a medical navigation system 205, the medical navigation system 205 typically must acquire and maintain a reference of the location of the tools in use as well as the patient in three dimensional (3D) space. In other words, during a navigated neurosurgery, there typically needs to be a tracked reference frame that is fixed relative to the patient's skull. During the registration phase of a navigated neurosurgery, e.g., the step 406, a transformation is calculated that maps the frame of reference of preoperative images, e.g., MRI or CT imagery, to the physical space of the surgery, such as the patient's head. This may be accomplished by the navigation system 205 tracking locations of fiducial markers fixed to the patient's head, relative to the static patient reference frame. The patient reference frame is typically rigidly attached to the head fixation device, such as a Mayfield™ clamp. Registration is typically performed before the sterile field has been established, e.g., the step 410.

Still referring back to FIGS. 4A and 4B and referring back to FIG. 3, an example informatics system is now described. The informatics system may be more specifically a health imaging informatics system and/or a surgical informatics system, although the present disclosure will refer to an informatics system generally, for simplicity. The informatics system may be used as part of pre-operative treatment planning, as part of intra-operative treatment planning and guidance, and for tracking post-operative results, for example. The informatics system may be implemented as a central control and processing system, e.g., a central computer or server system, similar to the control and processing system 300. In various examples, the disclosed informatics system may serve as a surgical informatics system that can store, filter, process, and serve a large amount of data in a manner that may be utilized to support clinical decisions by providing the surgeon with more accessible, clearer data in a real-time context. By enabling more informed decisions, the present disclosure may enable improvements in patient outcomes and/or reductions in healthcare costs. In some examples, the informatics system may implement elements from both the traditional "imaging informatics" and "surgical informatics" systems, in order to consolidate, connect, and present large quantities of image and non-image data in a scalable and pragmatic way. The present disclosure describes an example of the informatics system in the context of minimally invasive neurosurgery, however the present disclosure may be extensible to and/or be designed to accommodate other surgical procedures, e.g., via plug-ins.

Figure 5A:
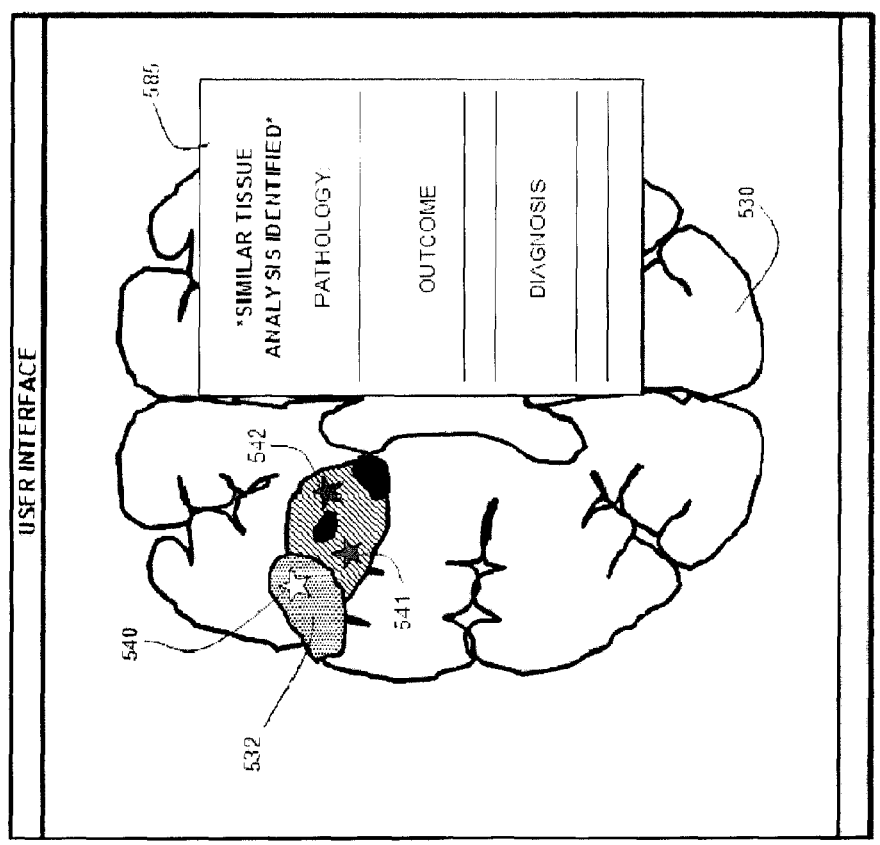
FIG. 5A is a diagram illustrating at least one selectable display, in a user interface, wherein tissue analysis information is provided by an example of the disclosed informatics system.
Figure 5B:
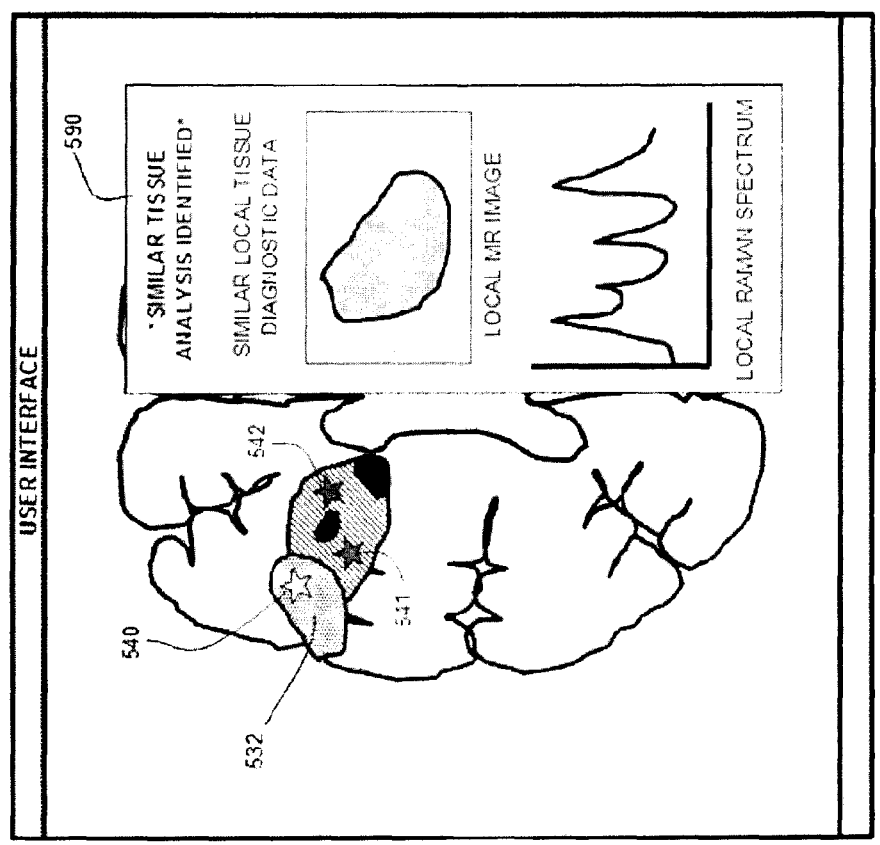
FIG. 5B is a diagram illustrating at least one selectable display, in a user interface, showing tissue analysis information provided by an example of the disclosed informatics system.

Referring to FIGS. 5A and 5B, together, these diagrams illustrate other informatics systems 700 for diagnosing a pathology, in accordance with other embodiments of the present disclosure. Referring to FIG. 5A, this diagram illustrates an example user interface provided by the informatics system 700. The example display provides the user with information pertaining to one or more similar tissue analyses, e.g., based on a comparison with historical data, as described above, and may be provided in response to the selection of a reference marker in a current image. The user interface displays an image of a patient's brain 530, including a tumor 532. The image may be obtained using any suitable imaging modality, such as MR. The user interface may be displayed in real-time as the patient's brain is being examined, e.g., as part of a tissue sampling procedure. The image may include one or more reference markers 540, 541, 542, which may correspond to locations of interest, e.g., locations where tissue samples were obtained. An overlay 585 is rendered on the display when a reference marker 540 is selected. In response to this selection, the informatics system 700 automatically compares data associated with tissue at the location of the reference marker 540 with historical tissue data. The overlay 585 may show the results of this comparison, including various forms of tissue information pertaining to one or more similar historical tissue analyses. The tissue information that may be displayed include pathology data associated with similar prior tissue analyses, outcome data associated with similar prior tissue analyses, and/or diagnosis data associated with similar prior tissue analyses, among others.

Referring to FIG. 5B, this diagram illustrates another example of the overlay 590, in which local tissue diagnostic data associated with similar historical tissue analyses may be presented to the user, in accordance with an embodiment of the present disclosure. As noted above, in some embodiments, tissue information pertaining to prior tissue analyses may be provided, based on a determination of similarity, e.g., using suitable comparison algorithms. The determination of similarity may be based not only on the tissue data, but also other information related to the procedure, such as patient age and/or hospital site. The determination of similar historical data may be based on a comparison between local tissue diagnostic data associated with the current patient, and historical local tissue diagnostic data obtained from a historical tissue analysis database.

Figure 5C:
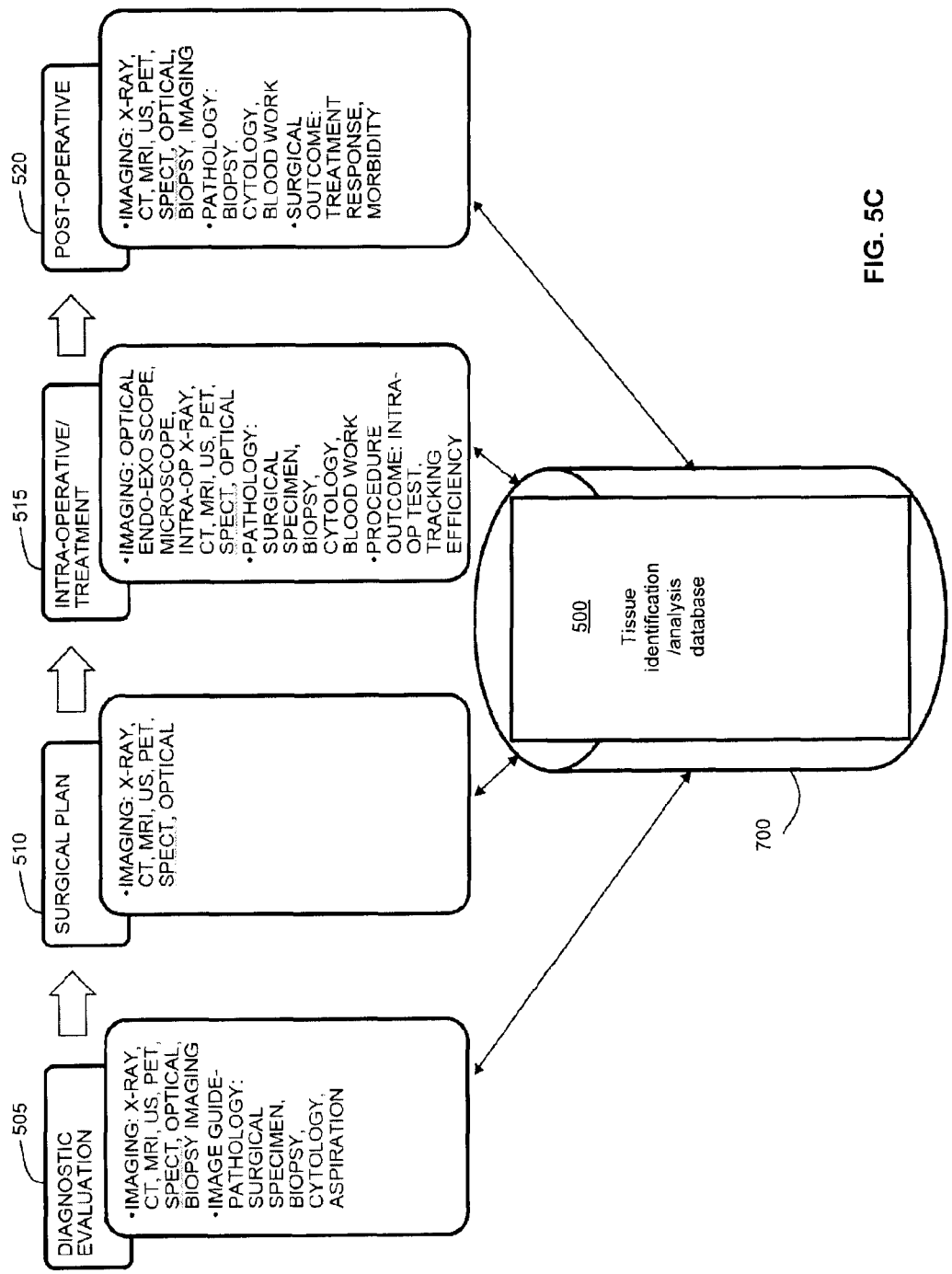
FIG. 5C is a workflow diagram illustrating an example system involving four aspects of patient care.

Referring to FIG. 5C, this workflow diagram illustrates an example of different stages of a surgical procedure, and their association to one or more tissue analysis databases, in accordance with an embodiment of the present disclosure. The figure shows an example embodiment involving four stages of decision-making, namely diagnostic evaluation 505, surgical planning 510, intra-operative surgery, diagnosis or treatment 515, and postoperative analysis 520. These stages are shown in their relation to each other, and with regard to the informatics system 700, which can be accessed during one or more stages of a medical procedure. In the example shown, informatics system 700 may include a tissue identification/analysis database 500, storing historical tissue identification and analyses. In some examples, the tissue identification/analysis database 500 may be remote from the informatics system 700 and may be queried by the informatics system 700 when appropriate. In this example, four aspects of patient care, where the use of a database linking registered imaging, pathology and outcomes can be utilized to improve diagnosis, surgical planning, surgical tissue differentiation and treatment and postoperative decision-making.

Still referring to FIG. 5C, the diagnostic modalities listed, include, but are not limited to, a set of whole organ, regional, or local diagnostic modalities, which may include imaging modalities such as, magnetic resonance Imaging (MRI), computerized tomography (CT), positron emission tomography (PET), SPECT, ultrasound (US), x-ray, optical (visible light or sections of full EM spectrum), optical coherence tomography (OCT), photo-acoustic (PA) or regional imaging modalities. These modalities can be acquired and shown as 1D, 2D, 3D, or 4D (3D+time), data sets, and may be registered to the patient in a dimensionally and positionally accurate manner. Biopsy methods include core or endoscopic biopsy, surgical biopsy (large section), aspiration, or other methods of removing tissue of interest for further pathology analysis.

Referring to FIG. 6, this flowchart illustrates a method for correlating a local tissue diagnostic measurement with historical tissue analysis data, in accordance with an embodiment of the present disclosure. This method is performed by the pathology correlator 726 of the data processing engine 720, for example. The example method may be carried out real-time during a procedure. At step 600, local tissue diagnostic data is obtained. The local tissue diagnostic data may be associated with one or more local tissue diagnostic measurements performed on a subject. For example, the local tissue diagnostic data may be local imaging data, such as a MR image obtained via an insertable MR probe, or local non-imaging data, such as locally measured Raman spectrum. In cases where this local tissue diagnostic data may not be sufficient to perform tissue analysis, the informatics system 700 may retrieve additional information, e.g., other information about the same patient, from other databases to supplement and complete the diagnostic data. For example, the informatics system 700 may perform correlation of the local tissue diagnostic data with historical local tissue diagnostic data from prior tissue analyses from the same or other patient. In cases in which the local tissue diagnostic data pertains to measurements made with more than one diagnostic modality, the location at which each local tissue analysis is made may be recorded, optionally along with a time stamp. The location information may be employed to correlate local tissue diagnostic data obtained for a common tissue location, but with different diagnostic modalities, for example.

Still referring to FIG. 6, at step 605, historical local tissue diagnostic data and tissue analysis data associated with one or more prior local tissue analyses is accessed, e.g., from the tissue identification/analysis database 500, or otherwise obtained. Tissue analysis data may include information including, but not limited to, one or more of pathology data, outcome data, tissue identification data, and/or diagnosis data. At step 610, the local tissue diagnostic data associated with the one or more local tissue diagnostic measurements, and the historical local tissue diagnostic data associated with the one or more prior local tissue analyses, may be compared. The comparison may be performed according to certain similarity criteria, such as similarity of region of interest, e.g., target surgical site, similarity of patient characteristics, and similarity of diagnostic data. Appropriate algorithms, e.g., nearest neighbor, are used by the data processing engine 720 to carry out such comparisons. The historical tissue diagnostic data may be searched for a close match with the current tissue diagnostic data. The search may be limited to historical data from the same diagnostic modality as the current data. Non-limited example of diagnostic modalities include MRI (T1, T2, DWI, ADC, FA, SWI, MRS), CT, Ultrasound, SPECT, PET, Raman spectroscopy, OCT, histological staining and high resolution optical imaging (microscopy and otherwise). For example, if the local tissue diagnostic data obtained for the subject includes a Raman spectrum, the tissue identification/analysis database 500 may the searched to find historical local tissue diagnostic data that was also measured via Raman spectroscopy (where the archived Raman spectra are stored correlated with tissue analysis data), and the measured Raman spectrum for the current patient may be compared with the historical Raman spectrum to find a prior tissue analysis having a similar Raman spectrum.

Figure 12:
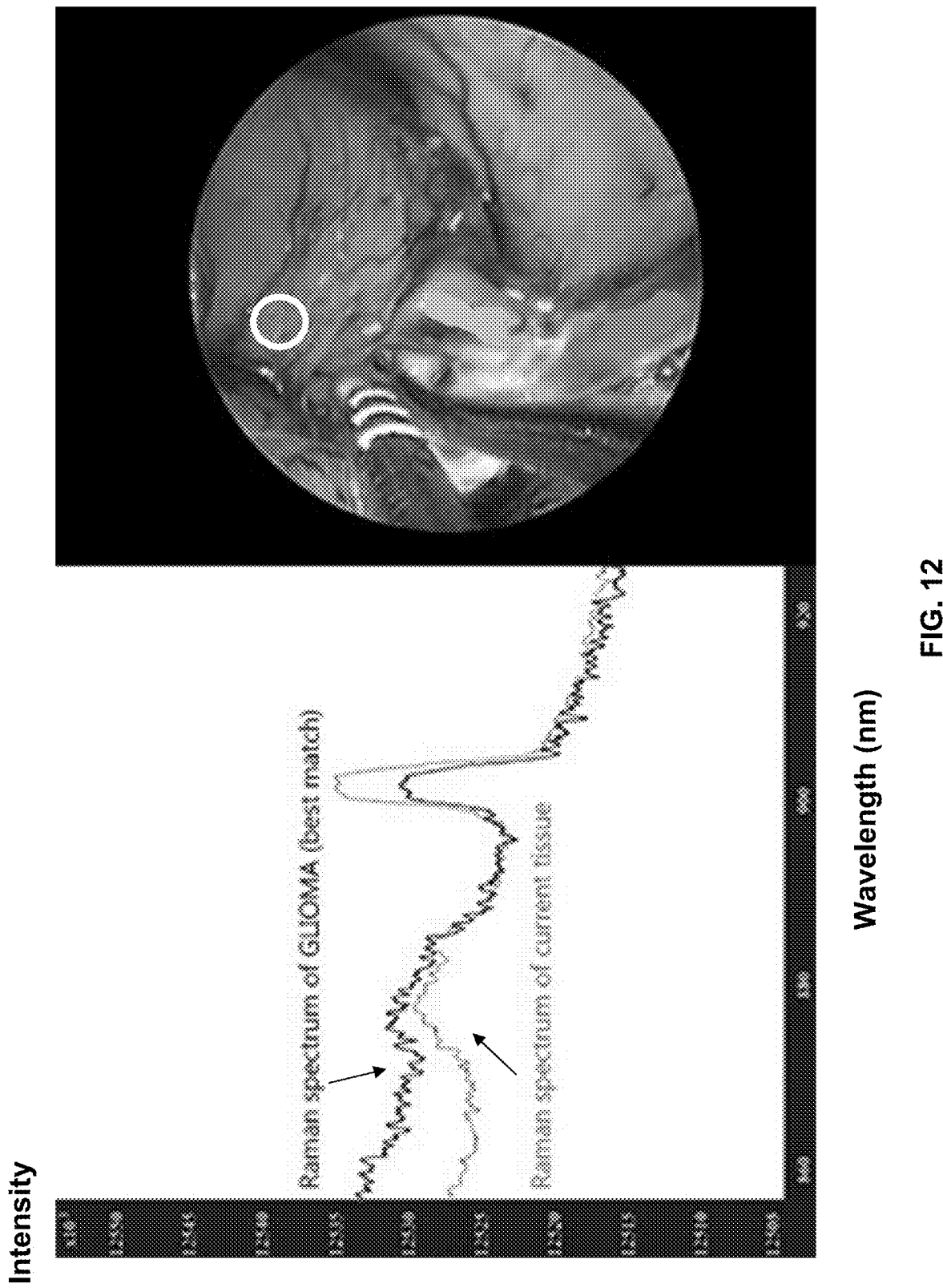
FIG. 12 is a rendering on a display of an example of a user interface provided by an example of the informatics system, showing a provision of intra-operative information.

Still referring to FIG. 6, at step 615, one or more historical local tissue analyses associated with one or more closest matching tissue diagnostic data are identified, thereby identifying a prior tissue analysis that may relevant to analysis of the local tissue region of the current subject. Information about the closest matching historical tissue identification, diagnosis and/or analyses may be outputted to the user, for example as a visual display, e.g., the user interfaces (FIGS. 12, 5A and 5B). Generally, data in the tissue identification/analysis database 500 may be the result of multiple tissue analyses, e.g. for the same subject, or for different subjects, stored in the data base 500 (or other suitable data structure) as local tissue diagnostic data obtained from local tissue diagnostic measurements and associated tissue analysis data. For example, one entry in the tissue identification/analysis database 500 may be constructed as follows, in which multiple diagnostic modalities are employed to interrogate a local tissue region of a subject (although it will be understood that an entry or data element may include diagnostic data from a single diagnostic modality). In the present example, three different diagnostic modalities are employed. A tracked Raman spectroscopy probe is employed to correlate the location the local tissue region with its Raman spectrum. Intra-operative MRI may also be employed to obtain MRI diagnostic data, where the use of a tracking and/or navigation system will allow the obtained MRI data to be correlated with the Raman spectrum. Finally, a tracked optical imaging device may be employed to optically interrogate the local tissue region, allowing the visual appearance of the tissue to be correlated with the Raman and MR data.

Still referring to FIG. 6, the local tissue diagnostic data associated with these measurements is stored, in the database 500 (or other suitable data structure), along with, or correlated with, tissue analysis data pertaining to the local region. The tissue analysis data may include pathology data. For example, if a tissue sample from the local tissue region is excised and sent to a pathology laboratory, the pathology results (which may include cell type, microscope image, tissue imaging (for example, X-ray, MRI)) may be correlated, as tissue analysis data, with the local tissue diagnostic data that was intra-operatively obtained, and stored as an entry in the tissue database 500. As described below, other types of tissue analysis data may additionally or alternatively be correlated with the local tissue diagnostic data to form the entry, e.g. database element, of the tissue analysis database 500. Examples of other tissue analysis data include, but are not limited to, outcome data, e.g. pertaining to the outcome of a medical procedure during which the local tissue diagnostic data was obtained, diagnosis data, e.g. pertaining to the diagnosis of a given pathology, and additional data pertaining to the subject, such as, but not limited to, demographic data, genetic data, and/or medical history data. In some example embodiments, the diagnostic data from two or more different diagnostic modalities may be employed allow for improved tissue analysis, as the same tissue region can be measured using multiple tissue analyses.

Still referring to FIG. 6, the tissue identification/analysis database 500, which, as noted above, includes tissue analysis data from prior tissue analyses, may be used by the informatics system 700 to guide, or suggest, which diagnostic modalities should or could be employed when performing medical procedures, e.g. surgical tissue resection procedures, involving known types of tissue. For example, if tissue resection of a known tissue type, e.g. a known tumor type, is to be performed, then the informatics system 700 queries the tissue identification/analysis database 500 to identify any prior tissue analyses corresponding to the particular tissue type of interest, in order to identify diagnostic modalities that have been shown to have local tissue diagnostic data that is correlated with a given tissue type. The identified diagnostic modalities may then be employed by the surgeon during the tissue resection procedure, and the local tissue diagnostic data that is intra-operatively obtained may be compared with the archival local tissue diagnostic data to intra-operatively identify exposed tissue. In some examples, the tissue identification/analysis database 500 may include only tissue diagnostic data that is correlated with the tissue analysis data, e.g. such that local tissue diagnostic data that did not show features or a signature associated with the tissue type is excluded.

Figure 7:
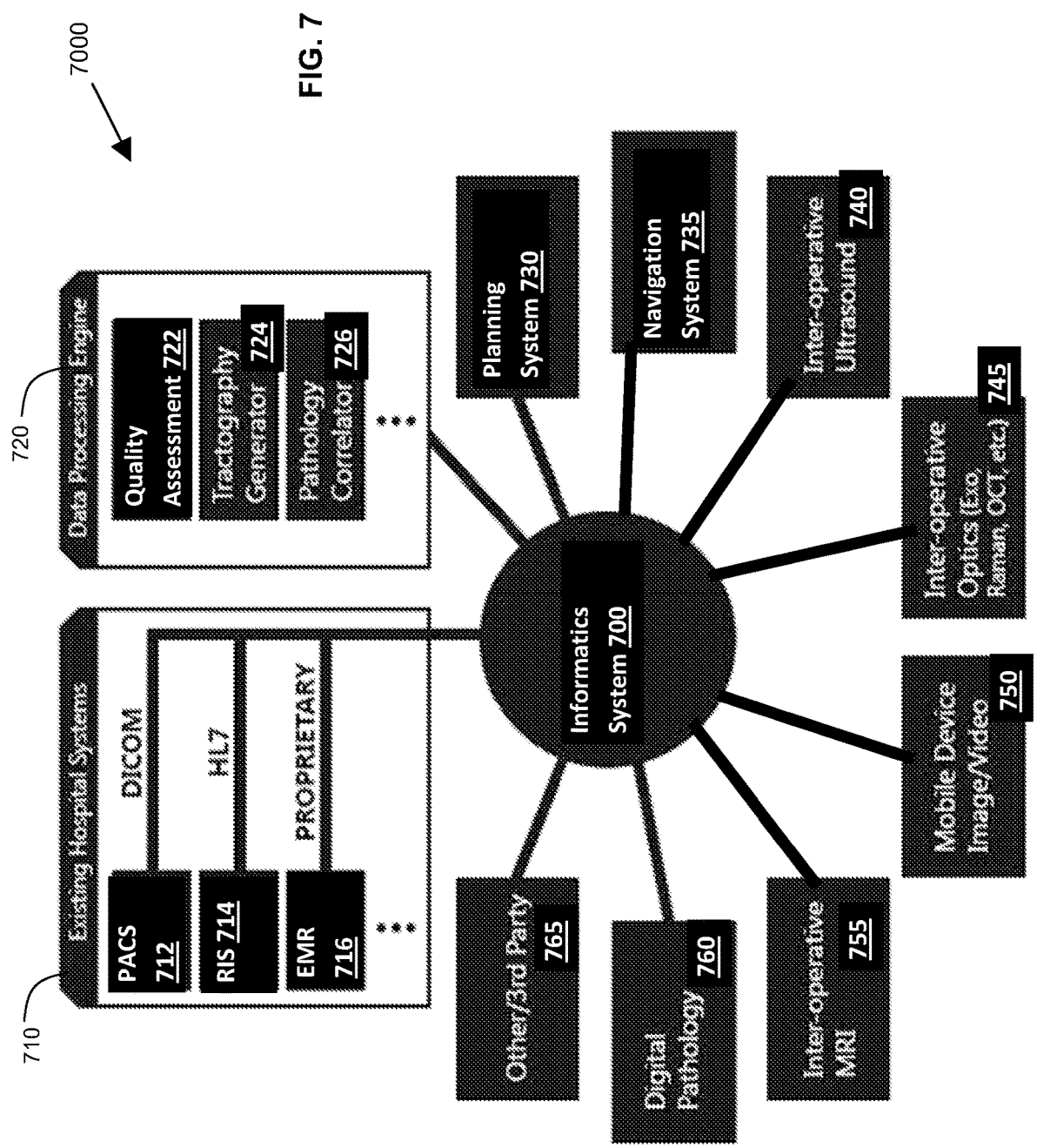
FIG. 7 is a diagram illustrating a manner in which an example of the disclosed informatics system communicates with various other information sources.

Referring to FIG. 7, this diagram illustrates a manner in which an example informatics system 700, as disclosed herein, may integrate and manage information from a variety of sources, in an overall health system 7000, in accordance with an embodiment of the present disclosure. The informatics system 700 is in communication with various data sources to transmit and/or receive information relevant to a patient's treatment. Although not specifically indicated, understood is that such communication may be two-way, may be wired or wireless communication, e.g., via wired or wireless networks, such as via an intranet or via the Internet, may be via removable and fixed media, and may take place over secure communication channels.

Still referring to FIG. 7, the informatics system 700 may communicate with existing conventional hospital information systems 710. Existing hospital systems 710 may include databases such as picture archiving and communication system (PACS) 712, radiology information system (RIS) 714 and electronic medical records (EMR) 716. The EMR 716, or other databases (not shown) of the hospital system 710 may store information specific to a given patient treatment, such as the pathology treated, the treatment plan used, lab testing carried out, and the treatment outcome, for example. The databases in the hospital system 710 may communicate data each in a different format. For example, PACS 712 may store only DICOM images, RIS 714 may store data according to the HL7 standard, and EMR 716 may store data in the hospital's own proprietary format.

Still referring to FIG. 7, the PACS 712 has served as the primary database and access point for surgical images. However, it is typically designed in a way that limits its use in informatics, such as: (a) it is typically a flat database, (b) it typically only stores DICOM images, and (c) its typical primary purpose is to be an archive of images for radiology. The informatics system 700 may be used to supplement PACS 712, and may provide information that is more tailored to the needs of surgical practitioners. For example, the informatics system 700 may: a) be a hierarchal database to facilitate grouping data by patient and operation, b) store DICOM images and additionally other file types, such as non-DICOM images, videos, PDFs, and XML documents, which may facilitate grouping image data with non-image data, and c) process data for both surgery and radiology to extract otherwise difficult-to-discern patterns. The informatics system 700 may serve as a hub for other data sources, including proprietary and non-proprietary data sources. As examples, data sources such as a planning system 730, navigation system 735, such as the navigation system 205, as shown in FIG. 2, inter-operative ultrasound 740, inter-operative optics, e.g., exoscope, Raman, optical coherence tomography (OCT), among others, mobile device images and/or videos 750, inter-operative imaging such as MRI 755, digital pathology 760 an other data sources, including third-party proprietary or non-proprietary sources 765.

Still referring to FIG. 7, the data communicated to/from the informatics system 700 may be of any suitable format, and the informatics system 700 may include modules or plug-ins to translate data formats for transmission to any given database. The informatics system 700 may push data to other databases, and may provide data to other databases in response to requests. Similarly, the informatics system 700 may query (or pull) other data sources for information, and other data sources may transmit data to the informatics system 700 without an explicit query. In some examples, the informatics system 700 may not receive a copy of the data, but rather may simply reference data that resides in other databases, which may be useful to reduce bandwidth usage. Referencing data may help avoid data duplication and re-entry. Such communication of data to/from the informatics system 700 may provide a rich set of data for analysis by a data processing engine 720 residing in or external to the informatics system 700, and below further described. The informatics system 700 may also help to integrate the existing workflow of a hospital system 710 across data sources. For example, the informatics system 700 may be able to track a RIS imaging order between the RIS 714 and imaging data sources such as inter-operative ultrasound 740. The informatics system 700 may communicate with one or more internal and/or external informatics databases (not shown) that may store identifying information, e.g., patient identification (ID), for tracking patient data across separate data sources, may store copies of data received from other data sources, and/or may store data in a hierarchy that can be defined in a way that is relevant for the data processing engine 720.

Still referring to FIG. 7, the informatics system 700 may also include a local historical database (not shown), which may store historical data about previous treatment plans, diagnoses, and outcomes, for example. Historical data may include, among others, treatment parameters, (\e.g., region of interest, patient age, pathology, treatment outcomes, pathology assessments, e.g., biopsy diagnoses, tissue sample diagnoses, and image data. In some examples, the informatics system 700 may, instead or in addition to a local historical database, access a remote historical database storing such historical data. The historical data may be cross-referenced to each other, for example such that the image data and tissue sample diagnosis for a given treatment plan are all cross-references and readily identifiable as being related to each other. The informatics system 700 may carry out data processing on historical data, for example using computer learning algorithms, in order to assist in characterizing and/or guiding planning and/or diagnosis of a current treatment, as described further below. The information stored in the historical database may be tracked, updated and utilized as an adaptive evaluation tool, to search for similar results, e.g., pathology, imaging and outcomes, in the history of the same patient, patients with similar imaging/clinical presentations. This historical database may include information, e.g., patient ID, to assist in correlation with other databases, e.g., EMR 716, storing patients' information and medical history.

Still referring to FIG. 7, once data is received by the informatics system 700, the data processing engine 720 may be automatically triggered to run various appropriate processing, e.g., implemented as plug-ins, on the data. The data processing engine 720 may host various data processing modules or engines to perform relevant data processing on the data. For example, the data processing engine 720 may include a quality assessment module 722 for performing quality assessment on image data, a tractography generator 724 to generate 3D models of neural tracts using data collected by diffusion tensor imaging (DTI), and a pathology correlator 726, among others. The pathology correlator 726 may perform pathology correlation to correlate molecular imaging data, e.g., OCT and Raman imaging, as well as intraoperative MR imaging, to pathology outcomes, as below further discussed. The data processing engine 720 may carry out data processing locally on the informatics system 700, or may be implemented in a figurative cloud of remote processors, for example.

Figure 8:
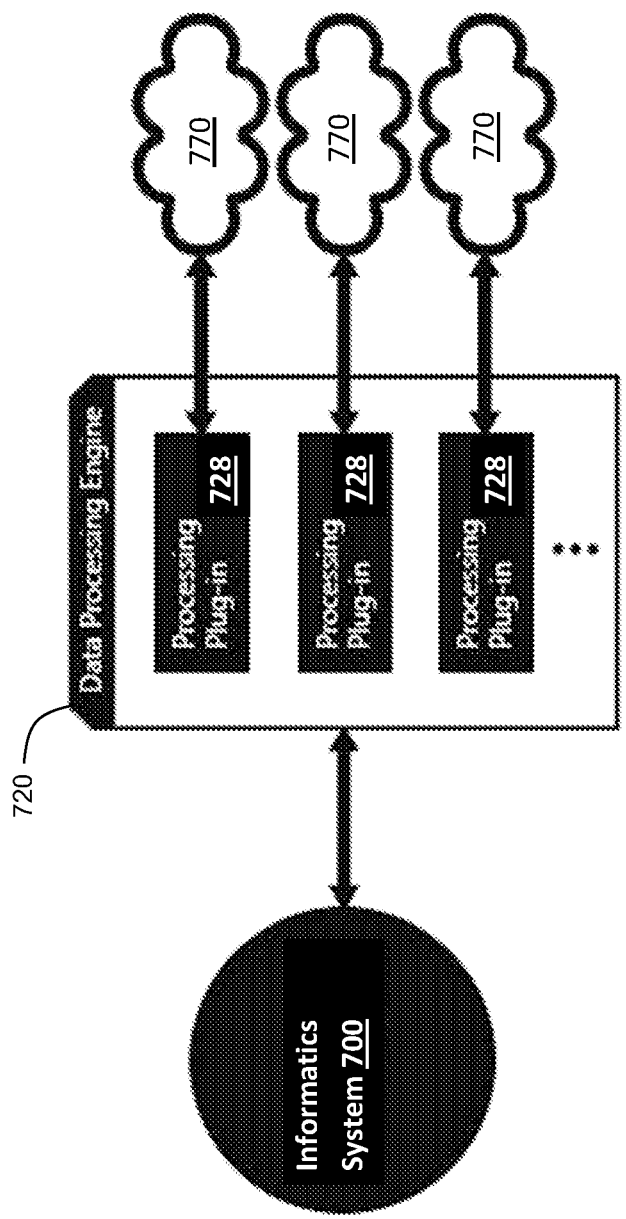
FIG. 8 is a diagram illustrating at least one plug-in useable by an example of the disclosed informatics system.

Referring of FIG. 8, this diagram illustrates a manner in which the data processing engine 720 may distribute data processing to multiple remote processors 770, via multiple processing plug-ins 728, as shown in FIG. 7, in accordance with an embodiment of the present disclosure. Where the data processing engine 720 is implemented remotely, this may allow for intense processing to be carried out by remote processors 770 separate from the informatics system 700, so that the processing resources of the informatics system 700 itself are not overly consumed, thus allowing the informatics system 700 to remain responsive to subsequent user interaction. The data processing engine 720 may also be implemented using parallel processing across multiple processors 770, which may allow certain processing tasks to be completed in a fraction of the time that it would take to perform them on a single processor. This may enable results to be available to clinicians sooner. The ability to provide results sooner may be of value during intra-operative image analysis, where OR time is at a premium.

Figure 9:
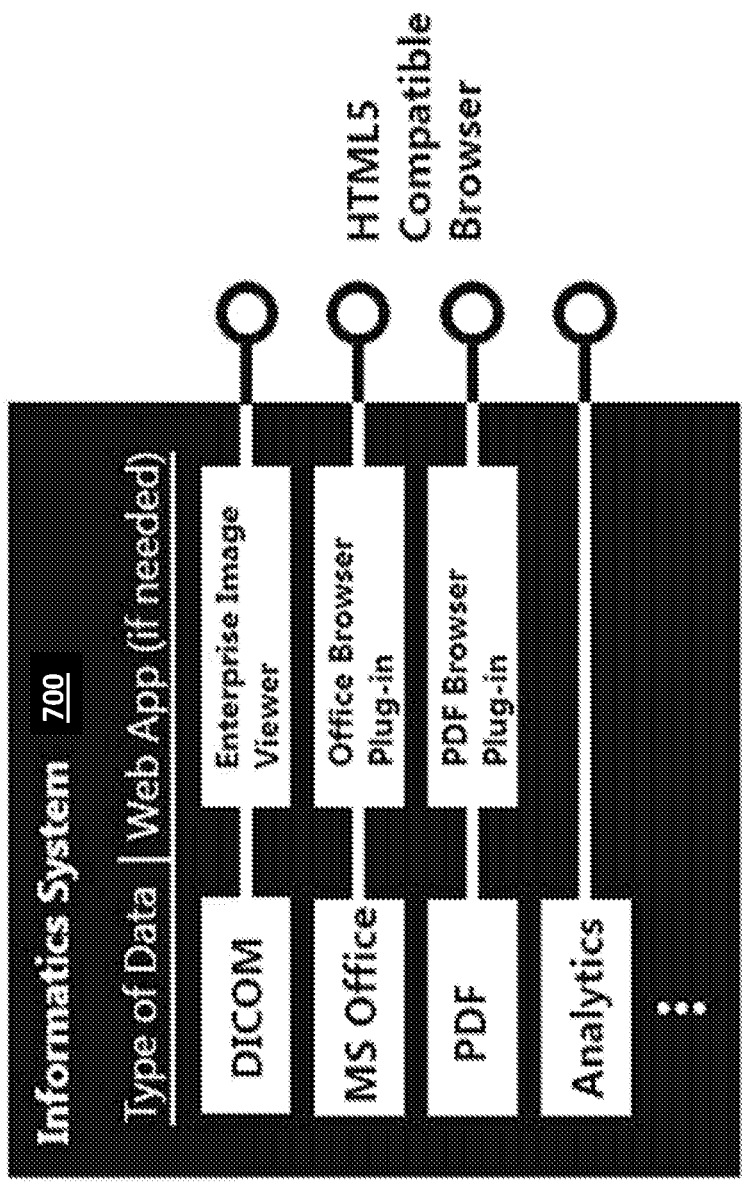
FIG. 9 is a diagram illustrating at least one plug-in useable by an example of the disclosed informatics system.

Referring to FIG. 9 this diagram illustrates a manner in which the data processing engine 720 may distribute data processing to multiple remote processors 770, via multiple processing plug-ins 728, as shown in FIG. 7, in accordance with an embodiment of the present disclosure. In some examples, the informatics system 700 may provide output from the data processing (and optionally the raw data from the data sources) to the user, e.g., the surgeon, via a web portal, such as an integrated, thin client web viewers, e.g., an enterprise DICOM viewer or a Microsoft Office document viewer, in accordance with an embodiment of the present disclosure. FIG. 9 illustrates an example of how the informatics system 700 may implement a web portal. In the example shown, the web portal may be provided via a HTML5-compatible browser, which may be accessible by desktop and/or mobile devices. The informatics system 700 may include plug-ins to enable output of various data types via the web portal. For example, the informatics system 700 may include an enterprise image viewer, a Microsoft Office browser plug-in, and a PDF browser plug-in to enable viewing of DICOM images, Microsoft Office documents, and PDF documents, respectively, via the web portal. The informatics system 700 may also provide output that may be directly outputted to the web portal, such as analytics generated by the data processing engine 720.

Referring back to FIG. 7, the web portal may also be used by the user to carry out a search of data stored by the informatics system 700, for example using a Lucene-based search. The web portal may also enable the user to carry out a search of other data sources that is in communication with the informatics system 700. In some examples, the informatics system 700 may not be directly accessible by a user. Rather, the informatics system 700 may only receive input from and provide output via another existing data source, such as via the planning system 730 or the navigation system 735. This may help to restrict user access to the informatics system 700, for security and privacy purposes, and may also provide the user with a more seamless integration of information without overwhelming the user. The informatics system 700 may serve to present information to the user in a unified format, for example by presenting results (also referred to as "analytics") after processing by the data processing engine 720. Such information may be presented in a single, user-friendly web page, for example.

Still referring back to FIG. 7, although certain plug-ins and modules have been described, understood is that these are non-limiting examples. Any suitable processing and/or data presentation modules and/or plug-ins may be implemented, and modules and/or plug-ins may be updated, added or removed dynamically. Certain modules that are considered clinically relevant in a certain medical context may be provided with an informatics system for that medical context. For example, a neurosurgical informatics system may include modules and plug-ins for managing and interpreting pre-operative, intra-operative, and post-operative imaging data across multiple patients and procedures, as in the examples described below. In an example informatics system 700 suitable for a neurosurgical context, the data processing engine 720 may include a module for archiving the target and entry locations for a neurosurgical procedure, and a module for comparing pre- and post-operative white matter tractography generated from MR DTI acquisitions. Such data analysis may: provide the surgeon with real-time, historical target/entry information to assist in treatment planning; to visualize and evaluate tissue preservation of important nerve fiber bundles following a neurosurgical procedure, while indicating the entry points that were used; and possibly to enable determination of correlations between changes in the patient's tractography and patient outcome. Such data analysis may be relevant to procedures such as minimally invasive ICH management and tumor resection.

Figure 10A:
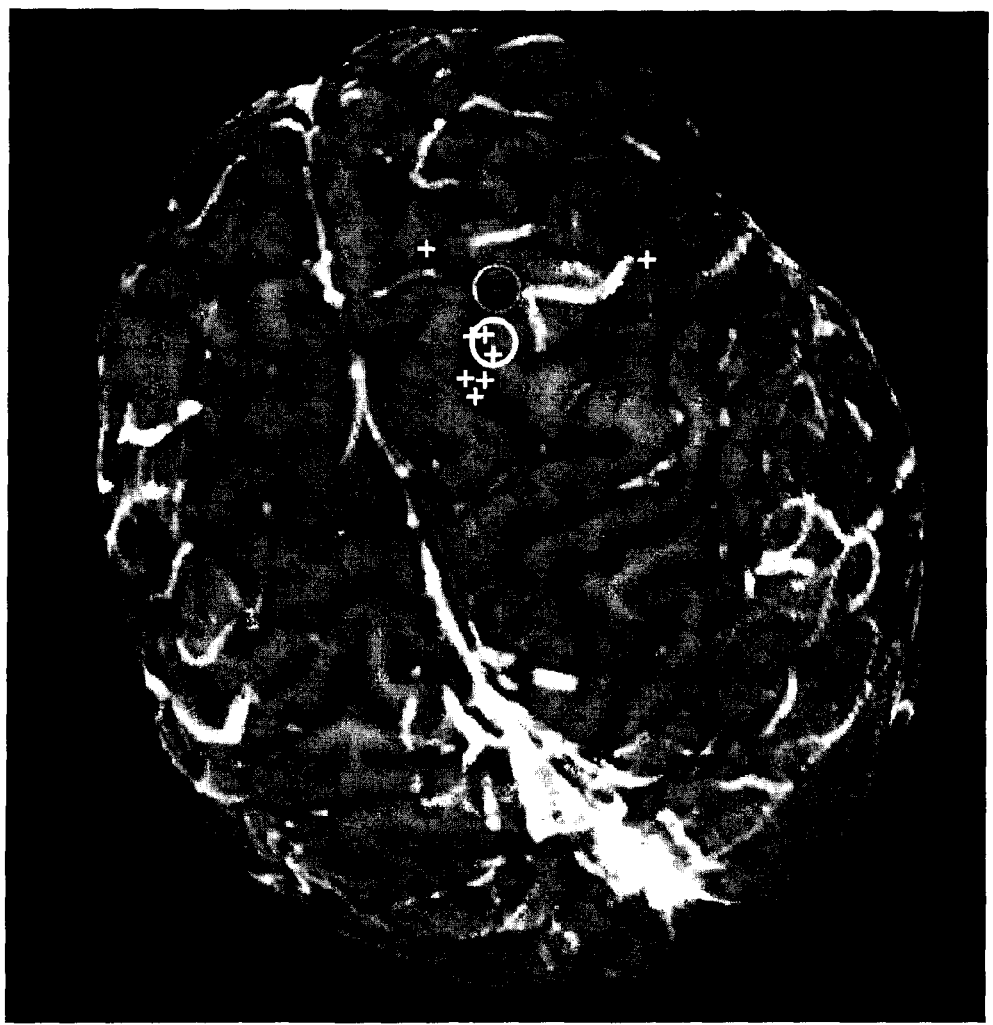
FIG. 10A is an image showing an example of a user interface provided by an example of the disclosed informatics system, to provide information during treatment planning.

Referring to FIG. 10A, this diagram illustrates an example user interface that may be provided by the informatics system 700, to assist in treatment planning for a neurosurgical procedure, in accordance with an embodiment of the present disclosure. This output may be provided to the user via a web portal, or integrated into conventional treatment planning systems, e.g., via an appropriate plug-in provided by the informatics system 700. in this example, the treatment planning involves planning an entry point to access a surgical target within the brain. The user interface of FIG. 10A shows an image of the patient's brain, with indicators (in this example, '+' symbols) indicating historical entry points for accessing the same or similar targets in historical treatment plans. The circle indicates the user's currently selected entry point.

Figure 10B:
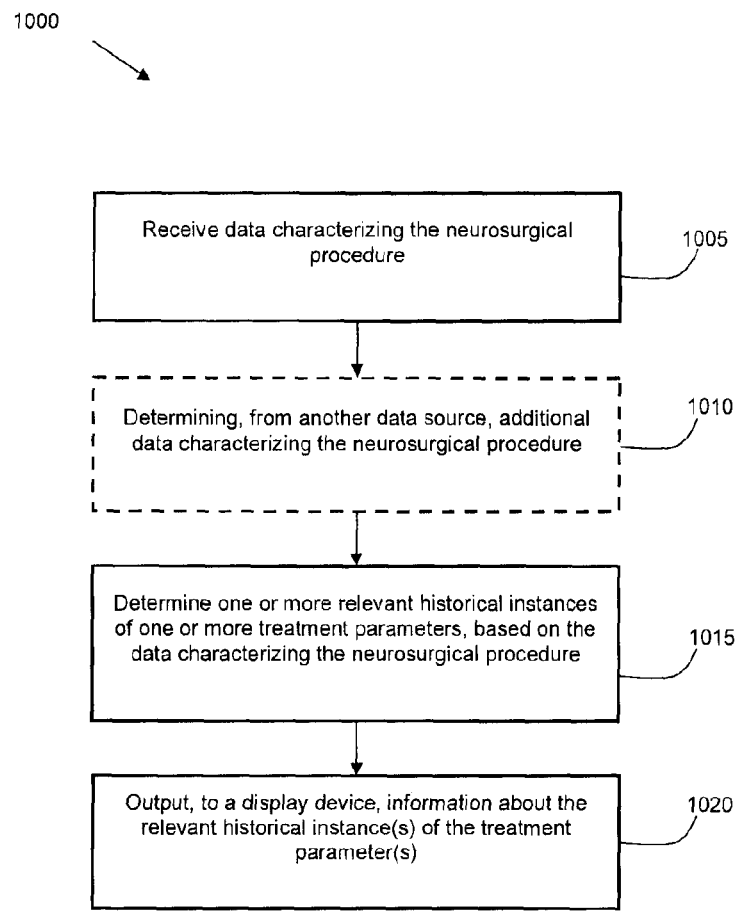
FIG. 10B is a flowchart illustrating an example method for treatment planning, using an example of the informatics system.

Referring to FIG. 10B, this flowchart illustrates an example method 1000 for providing assistance during treatment planning for a neurology procedure, e.g., a surgical procedure or a drug treatment, in accordance with an embodiment of the present disclosure. Generally, throughout the present disclosure, neurology procedure may refer to surgical as well as non-surgical procedures. For simplicity, examples will be described with reference to a neurosurgical procedure and surgical treatment plane. However, understood is that surgical and non-surgical procedures may both be possible. The method 1000 may be implemented using a treatment planning module of the data processing engine 720. Generally, steps described below as being carried out by the informatics system 700 may more specifically be implemented using a module of the data processing engine 720.

Still referring to FIG. 10B and referring back to FIG. 4A, in some examples, the method 1000 may be provided intra-operatively as part of the craniotomy procedure, e.g., at block 414 (FIG. 4A), or pre-operatively and the plan imported, e.g., at block 402 (FIG. 4A). A user may interact directly with the informatics system 700 (e.g., via a web portal) to initiate the method 1000, or the interaction may be via a planning system 730. For example, as a user creates a treatment plan using the planning system 730, the planning system 730 may automatically interface with the informatics system 700 to access analytics to assist in treatment planning. In some examples, the interface between the planning system 730 and the informatics system 700 may be entirely hidden from the user, such that the user input to the planning system 730 is the same as if the informatics system 700 were absent. The informatics system 700 may receive a set of data characterizing the neurosurgical procedure. For example, the informatics system 700 may receive data from the planning system 730 indicating the patient, e.g., a patient ID, and the region of interest or target site, e.g., a tumor site within the brain.

Still referring to FIG. 10B, optionally, at block 1010, the informatics system 700 determines additional data characterizing the neurosurgical procedure. This occurs when the data received at block 1005 is insufficient for treatment planning. For example, the informatics system 700 may query one or more image data sources, e.g., PACS 712, inter-operative MRI 755, inter-operative optics 745, and/or inter-operative ultrasound 740, to retrieve image data relevant to the site of the neurosurgical procedure. A patient ID may be used to identify the relevant image data from the image data sources, for example. The informatics system 700 may also query the EMR 716 to determine other patient information, e.g., patient age and treatment history, that may impact the treatment planning. The informatics system 700 may analyze the various data characterizing the neurosurgical procedure and generate a subset of data, e.g., patient age, patient gender and target site, characterizing the neurosurgical procedure.

Still referring to FIG. 10B, at block 1015, the informatics system 700 may determine any relevant historical data, such as historical treatment plans, based on the subset of data characterizing the neurosurgical procedure. Generally, the term "historical" may be used in the present disclosure to refer to any treatment plan previous to the treatment being currently planned. Determination of historical treatment plans may be carried out by the informatics system 700 querying its own database of historical data and/or databases belonging to one or more hospital systems 710. Generally, historical treatment plans may include treatment plans that were carried out previously for the current patient or a different patient, and at the same hospital site or another hospital site.

Still referring to FIG. 10B, for example, the informatics system 700 may determine all historical treatment plans that match the patient age, patient gender, pathology conditions and region of interest. In some examples, the informatics system 700 may also filter historical data based on treatment outcomes, such that only treatment plans associated with desirable treatment outcomes are considered. In some examples, a nearest neighbor algorithm may be carried out to determine which historical treatment plans are relevant, e.g., to determine treatment plans with similar regions of interest to the currently planned treatment. This may be more practical than searching for a strict match, since it is unlikely for a historical treatment plan to match all characteristics of the current neurosurgical procedure.

Still referring to FIG. 10B, from the relevant historical treatment plans, the informatics system 700 may extract one or more treatment parameters that may assist in treatment planning. For example, the informatics system 700 may extract the sulcal entry point from the relevant historical treatment plans. In another example, the informatics system 700 may determine, for a current treatment targeting the corpus callosum, one or more historical trajectories associated with positive patient outcomes. Although historical treatment plans have been described, the historical data may include other historical data not in the form of treatment plans, for example historical outcomes.

Still referring to FIG. 10B, at block 1020, the extracted historical treatment parameters may be outputted to a display device, e.g., a display screen of the planning system 730. In some examples, the output may be in the form of a user interface, such as shown in FIG. 10A, where the historical treatment parameters are displayed together with the currently planned treatment parameter. This may enable the user to easily evaluate whether the current treatment plan is in line with previous treatment plans. In some examples, the output may be integrated with the output normally provided by the planning system 730. For example, the historical treatment parameters may be displayed superimposed on a conventional image showing the current treatment plan. In some examples, particular historical treatment parameter values, e.g., particular historical entry points, associated with particularly desirable patient outcomes may be emphasized, e.g., highlighted or colored in green.

Still referring to FIG. 10B, since treatment planning may take several stages, e.g., planning entry point, then planning cannulation trajectory, the method 1000 may be repeated at each treatment planning stage, and for each planned treatment parameter. As illustrated in the example above, the informatics system 700 may help the user to visualize and understand correlations between data from separate data sources. In some examples, the informatics system 700 may provide quantification of traditional qualitative data, to further assist in analyzing this data.

Still referring to FIG. 10B, in some examples, the treatment planning guidance offered by the informatics system 700 may provide the user with recommended treatment parameters, e.g., based on relevant historical treatment parameters that are associated with positive patient outcomes. In other examples, the treatment planning guidance may be simply informative in nature, for example by filtering out historical data to only present the user with the most relevant historical treatment parameters, e.g., filtering according to the specific treatment type and/or treatment stage, filtering according to the specific patient or patient type, or by providing the user with a mapping of historical treatment parameters for different treatment target locations, without providing any recommendations.

Figure 11:
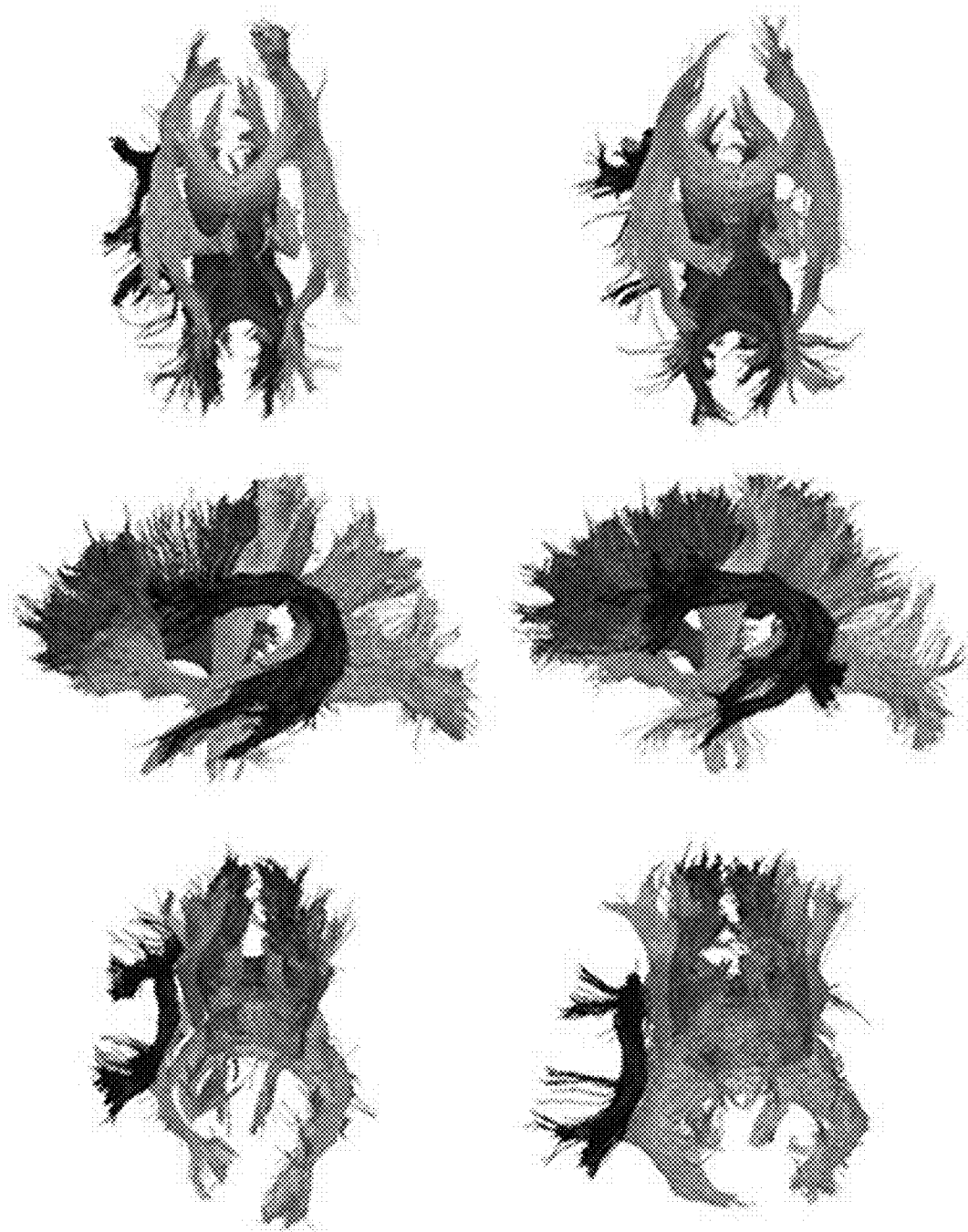
FIG. 11 is a set of images illustrating an example of how pre-operative and post-operative information is quantified and stored in an example of the disclosed informatics system.

Referring to FIG. 11, this set of images show an example of a manner in which pre-operative tractography information and post-operative tractography information are quantified, in accordance with embodiments of the present disclosure. The informatics system 700 may receive DTI data and use this data to generate a tractography, e.g., using the tractography generator 724 in the data processing engine 720, to visual represent a patient's neural tracts, both pre-operation and post-operation. The informatics system 700 may quantify the tractographs and perform a quantitative comparison of the pre-operation and post-operation tractographs. Each tractograph may be quantified by calculating the fiber volume of particular fiber bundles, such as the superior longitudinal fasciculus (SLF) and the arcuate fasciculus (AF). A quantitative comparison may then be made automatically. The informatics system 700 may also query other data sources, e.g., EMR 716, to determine the patient outcomes, e.g., vision, motor, cognition, memory, mortality, etc., associated with the post-operation tractograph. Similar quantification and comparisons may be performed for other patient measurements.

Still referring to FIG. 11, by providing the user with such information, the user may be provided with feedback for further surgical decisions, as well as valuable research data. In some examples, the informatics system 700 may be useful for tagging and correlating image data with pathological assessment. This may help the user to identify a pathology visible in a captured image, based on historical data. The informatics system 700 may provide the user with a unified visualization correlating image data with data associated with a tissue sample. This may be referred to as tagging an image with pathology information. For example, information about a tissue sample, e.g., patient ID, sample site, may be stored in the digital pathology database 760. The informatics system 700 may receive data from both the digital pathology database 760 and an image data source, e.g., inter-operative optics 745, and, using data correlation algorithms, e.g., comparing and matching patient ID, may mark, store, and provide visualization, e.g., as an indicator or overlay over a displayed image, of the location at which brain tissue was resected within pre-operative and/or intra-operative image data. This may allow clinicians to more accurately record and recall the anatomical region of a tissue sample, may help aid in ensuring that the appropriate tissue was resected, and may serve to categorize and file pathology results, to be used as input data to other data processing, for example.

Still referring to FIG. 11, pathology correlation may generally involve evaluating point, regional, and/or full image data. This may be carried out using the pathology correlator 726 of the data processing engine 720, for example. The pathology correlator 726 may also perform a similarity comparison, e.g., using appropriate algorithms, such as computer learning algorithms, against historical image data (typically from the same imaging modality), which may be retrieved from a historical database local to the informatics system 700 or from a remote database of historical image data, and which have been associated with known pathology, e.g., as a result of previous tagging operations, as described above. This image data may include data from various image data sources, such as Raman spectroscopy, OCT and hyperspectral imaging, and may also include intra-operative MR, for example. Such pathology correlation may be carried out by the informatics system 700 post-operatively and/or intra-operatively, e.g., during a biopsy procedure. if the current image data is determined, e.g., using similarity determination algorithms, to be a close enough match to historical image data, and that historical data has been tagged with a certain pathology, then the informatics system 700 may provide indication to the user that the current image data may share the same pathology. This may provide the user with insight as to what type of tissue they are currently looking at in an intra-operative context.

Referring to FIG. 12, this rendering in a display on an example of a user interface shows a result of a pathology correlation performed by the informatics system 700, in accordance with an embodiment of the present disclosure. The user may be provided with a real-time view of the tissue sample site (right image), with an indicator, e.g., a circle, showing the tissue sampled. The user may also be provided with an indicator of a likely pathology for the tissue sample, such as a comparison of the Raman spectrum of the current tissue sample with the Raman spectrum of the closest match in historical tissue samples (left image). In other examples, rather than providing a chart, the display may instead provide text or other visual indication of the likely pathology. This may be useful with Raman and OCT as these are real-time modalities, meaning a surgeon may be provided with quicker feedback regarding what type of tissue they are currently viewing. Thus, when a surgeon uses an OCT or Rama probe to analyze tumor tissue, for example, and tissue around the tumor margins, the informatics system 700 may use the resulting image signals as "signatures" to be compared against a database of image "signatures" of known pathologies. The surgeon may thus be provided with information from intraoperative analysis of the probed tissue, e.g., whether the tissue is healthy or diseased tissue. This may be useful for tumor resection procedures, for example, enabling a surgeon to probe the margins of the tumor to ensure that the margins are clean of tumor tissue.

Although the present disclosure describes the operation of the informatics system with certain data processing modules, it should be understood that the informatics system may include other modules. The informatics system may be repeated updated and/or modified by the update, addition and/or removal of modules. Generally, each module may provide the functions of scouring large amounts of data, and distilling them into user-friendly outputs.

Any information stored locally by the informatics system may be modified to anonymize the data, e.g., by removal of patient-sensitive data. This may be carried out automatically by the informatics system. When the informatics system presents information to a user, where the information may be derived from remote data sources, the presented information may be similarly anonymized.

The informatics system may serve as a central hub for multiple hospital sites, and may facilitate sharing of data across different hospital sites via the central hub. Alternatively, each hospital may have its own installation of the informatics system (and optionally each hospital may have more two or more installations of the informatics system, such as for different wings of the hospital), and the common platform offered by the informatics system may facilitate sharing of data across different hospital sites. Where there are two or more installations of the informatics system in operation in the health system, it may be possible to amalgamate or consolidate multiple installations of the informatics system together. This may be via an automated synchronization mechanism on each installation that propagates changes from a more recent installation or the older installation (or vice versa), or via a third installation that simply holds references to the two existing installations. This may result in a web-like or tree-like structure of multiple informatics systems.

The amalgamation of data via a central informatics system or a web/tree of informatics systems may facilitate collaboration between surgeons across different hospitals and even within the same hospital. This may enable knowledge and experience of a single surgeon to be accessible by multiple other surgeons. The present disclosure may also be used to provide training and/or proctoring, even remotely. Further, since the knowledge and experience of a surgeon may be distilled in the treatment of their patients, this knowledge and experience may be accessed (in the form of historical treatment plans) without undue burden on the surgeon.

Although the present disclosure discusses treatment planning for treatment of a brain tumor, in various examples, understood is that the present disclosure may be applicable to other surgical and non-surgical procedures. For example, embodiments of the present disclosure may be applicable to any neurology procedure, including surgical procedures, pharmaceutical treatments, and combination surgical/pharmaceutical treatments.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed:

1. A method of intraoperatively providing planning information for a neurosurgical procedure by way of an informatics system, the method comprising:

providing the informatics system, providing the informatics system comprising providing a central system, providing the central system comprising providing a data processing module and providing a processor operable by the data processing module, providing the data processing module comprising providing a planning module, providing a tractography generator to generate 3D models of neural tracts using diffusion tensor imaging data, providing a module for comparing pre-procedure tractography data with post-procedure tractography data generated from the diffusion tensor imaging data to enable determination of correlations between changes in the patient's tractography and patient outcome, and providing at least one plug-in configured to translate data formats for transmission to any given database and to enable output of a plurality of data types via a web portal;

receiving a first set of data characterizing the neurosurgical procedure by the central system;

accessing at least one historical database containing historical data about at least one historical procedure by the central system;

determining at least one set of historical data relevant to the neurosurgical procedure, based on a determination of similarity to the first set of data, by the central system;

determining, from the at least one set of historical data, at least one historical instance of at least one procedure parameter relevant to the neurosurgical procedure by the central system;

using the tractography generator, receiving diffusion tensor imaging data and generating the pre-procedure tractography data and the post-procedure tractography data from the diffusion tensor imaging data;

quantifying the pre-procedure tractography data and the post-procedure tractography data, quantifying comprising calculating a fiber volume of a particular fiber bundles in the pre-procedure tractography data and in the post-procedure tractography data;

automatically performing a quantitative comparison of the pre-procedure tractography data with the post-procedure tractography;

using the at least one plug-in, translating data formats for transmission to any given database;

causing an output device to display the quantitative comparison in combination with the pre-procedure image data and the post-procedure image data, the pre-procedure image data comprising pre-procedure tractography data and the post-procedure image data comprising post-procedure tractography data, and the quantitative comparison comprising a comparison of pre-procedure neural tract data in the pre-procedure tractography data with the post-procedure neural tract data in the post-procedure tractography data; and causing an output device to display the at least one historical instance of the at least one procedure parameter by the central system, the at least one procedure parameter comprising at least one historical entry site for the neurosurgical procedure, displaying comprising displaying at least one indicator of at least one location of the at least one historical entry site superimposed on an image of a region of interest of a current treatment plan for the neurosurgical procedure, thereby providing output via the web portal in at least one manner of directly outputting analytics and indirectly outputting translated data in at least one data type of the plurality of data types via the at least one plug-in.

2. The method of claim 1, further comprising:
accessing at least one of: at least one other local and at least one remote database;
determining additional data characterizing the neurosurgical procedure, the additional data being determined to be relevant to the neurosurgical procedure based on identification information included in the first set of data; and
including the additional data into the first set of data.

3. The method of claim 1,
wherein determining the at least one set of historical data relevant to the neurosurgical procedure comprises determining at least one set of historical data associated with tissue analysis data similar to tissue analysis data associated with the neurosurgical procedure, and
wherein determining the at least one historical instance of the at least one procedure parameter comprises determining at least one tissue diagnosis associated with the at least one set of historical data.

4. The method of claim 3, wherein the first set of data comprises image data associated with the neurosurgical procedure, the method further comprising receiving input selecting a location in the image data, and determining the at least one set of historical data relevant to the neurosurgical procedure based on tissue analysis data associated with the selected location.

5. The method of claim 1, wherein determining the at least one set of historical data relevant to the neurosurgical procedure comprises determining at least one set of historical data associated with image data similar to image data associated with the neurosurgical procedure.

6. The method of claim 1, further comprising displaying, on the output device, at least one procedure outcome associated with the at least one set of historical data.

7. An informatics system for intraoperatively providing information relating to a neurosurgical procedure, the informatics system comprising:
a central system comprising a processor operable by a data processing module, the data processing module comprising a planning module, a tractography generator to generate 3D models of neural tracts using diffusion tensor imaging data, a module for comparing pre-procedure tractography data with post-procedure tractography data generated from the diffusion tensor imaging data to enable determination of correlations between changes in the patient's tractography and patient outcome, the data processing module in communication with a plurality of databases, each of the plurality of databases storing different information associated with the neurosurgical procedure, and at least one plug-in configured to translate data formats for transmission to any given database and to enable output of a plurality of data types via a web portal,
the central system configured to:
receive a first set of data characterizing the neurosurgical procedure;
access at least one historical database containing historical data about historical procedures;
determine at least one set of historical data relevant to the neurosurgical procedure, based on a determination of similarity to the first set of data;
determine, from the at least one set of historical data, at least one historical instance of at least one procedure parameter relevant to the neurosurgical procedure, the at least one procedure parameter comprising at least one historical entry site for the neurosurgical procedure;
use the tractography generator to receive diffusion tensor imaging data and generate the pre-procedure tractography data and the post-procedure tractography data from the diffusion tensor imaging data;
quantify the pre-procedure tractography data and the post-procedure tractography data by calculating a fiber volume of a particular fiber bundles in the pre-procedure tractography data and in the post-procedure tractography data;
automatically perform a quantitative comparison of the pre-procedure tractography data with the post-procedure tractography;
use the at least one plug-in to translate data formats for transmission to any given database;
cause an output device to display the quantitative comparison in combination with the pre-procedure image data and the post-procedure image data, the pre-procedure image data comprising pre-procedure tractography data and the post-procedure image data comprising post-procedure tractography data, and the quantitative comparison comprising a comparison of pre-procedure neural tract data in the pre-procedure tractography data with the post-procedure neural tract data in the post-procedure tractography data; and
cause an output device to display the at least one historical instance of the at least one procedure parameter, including displaying at least one indicator of at least one location of the at least one historical entry site superimposed on an image of a region of interest of a current treatment plan for the neurosurgical procedure,
whereby output is providable via the web portal in at least one manner of direct output of analytics and indirect output of at least one translated data type of the plurality of data types via the at least one plug-in.

8. The system of claim 7, wherein the planning module further causes the system to:
access at least one of: at least one other local database and a remote database;
determine additional data characterizing the neurosurgical procedure, the additional data being determined to be relevant to the neurosurgical procedure based on identification information included in a first set of data; and
include the additional data into the first set of data.

9. The system of claim 8, wherein the first set of data includes image data associated with the neurosurgical procedure, the planning module further causes the system to receive input selecting a location in the image data, and determine the at least one set of historical data relevant to the neurosurgical procedure based on tissue analysis data associated with the selected location.

10. The system of claim 8, wherein the planning module further causes the system to determine the at least one set of historical data relevant to the neurosurgical procedure by determining at least one set of historical data associated with image data similar to image data associated with the neurosurgical procedure.

11. The system of claim 8, wherein the planning module further causes the system to cause the output device to display at least one procedure outcome associated with the at least one set of historical data.

12. The system of claim 7, wherein the planning module further causes the system to determine the at least one set of historical data relevant to the neurosurgical procedure by determining at least one set of historical data associated with tissue analysis data similar to tissue analysis data associated with the neurosurgical procedure, and to determine the at least one historical instance of the at least one procedure parameter by determining at least one tissue diagnosis associated with the at least one set of historical data.

13. The system of claim 7,
wherein the planning module further causes the system to: access at least one of: at least one other local database and a remote database; determine additional data characterizing the neurosurgical procedure, the additional data being determined to be relevant to the neurosurgical procedure based on identification information included in a first set of data; and include the additional data into the first set of data,
wherein the planning module further causes the system to determine the at least one set of historical data relevant to the neurosurgical procedure by determining at least one set of historical data associated with tissue analysis data similar to tissue analysis data associated with the neurosurgical procedure, and to determine the at least one historical instance of the at least one procedure parameter by determining at least one tissue diagnosis associated with the at least one set of historical data,
wherein the first set of data includes image data associated with the neurosurgical procedure, the planning module further causes the system to receive input selecting a location in the image data, and determine the at least one set of historical data relevant to the neurosurgical procedure based on tissue analysis data associated with the selected location,
wherein the planning module further causes the system to determine the at least one set of historical data relevant to the neurosurgical procedure by determining at least one set of historical data associated with image data similar to image data associated with the neurosurgical procedure, and
wherein the planning module further causes the system to cause the output device to display at least one procedure outcome associated with the at least one set of historical data.

14. A method of fabricating an informatics system for intraoperatively providing information relating to a neurosurgical procedure, the method comprising:
providing a central system comprising a processor operable by a data processing module, the processing module comprising a planning module, a tractography generator to generate 3D models of neural tracts using diffusion tensor imaging data, a module for comparing pre-procedure tractography data with post-procedure tractography data generated from the diffusion tensor imaging data to enable determination of correlations between changes in the patient's tractography and patient outcome, the processing module in communication with a plurality of databases, each of the plurality of databases storing different information associated with the neurosurgical procedure; and at least one plug-in configured to translate data formats for transmission to any given database and to enable output of a plurality of data types via a web portal, providing the central system comprising configuring the central system to:
receive a first set of data characterizing the neurosurgical procedure;
access at least one historical database containing historical data about historical procedures;
determine at least one set of historical data relevant to the neurosurgical procedure, based on a determination of similarity to the first set of data;
determine, from the at least one set of historical data, at least one historical instance of at least one procedure parameter relevant to the neurosurgical procedure, the at least one procedure parameter comprising at least one historical entry site for the neurosurgical procedure;
use the tractography generator to receive diffusion tensor imaging data and generate the pre-procedure tractography data and the post-procedure tractography data from the diffusion tensor imaging data;
quantify the pre-procedure tractography data and the post-procedure tractography data by calculating a fiber volume of a particular fiber bundles in the pre-procedure tractography data and in the post-procedure tractography data;
automatically perform a quantitative comparison of the pre-procedure tractography data with the post-procedure tractography;
use the at least one plug-in to translate data formats for transmission to any given database;
cause an output device to display the quantitative comparison in combination with the pre-procedure image data and the post-procedure image data, the pre-procedure image data comprising pre-procedure tractography data and the post-procedure image data comprising post-procedure tractography data, and the quantitative comparison comprising a comparison of pre-procedure neural tract data in the pre-procedure tractography data with the post-procedure neural tract data in the post-procedure tractography data; and
cause an output device to display the at least one historical instance of the at least one procedure parameter, including displaying at least one indicator of at least one location of the at least one historical entry site superimposed on an image of a region of interest of a current treatment plan for the neurosurgical procedure,
whereby output is providable via the web portal in at least one manner of direct output of analytics and indirect output of at least one translated data type of the plurality of data types via the at least one plug-in.

15. The method of claim 14, wherein providing the central system comprises providing the planning module further causing the system to:
access at least one of: at least one other local database and a remote database;
determine additional data characterizing the neurosurgical procedure, the additional data being determined to be relevant to the neurosurgical procedure based on identification information included in a first set of data; and
include the additional data into the first set of data.

16. The method of claim 15, wherein, providing the central system, the first set of data comprises image data associated with the neurosurgical procedure, providing the central system comprising providing the planning module further causing the system to receive input selecting a location in the image data, and determine the at least one set of historical data relevant to the neurosurgical procedure based on tissue analysis data associated with the selected location.

17. The method of claim 14, wherein providing the central system comprises providing the planning module further causing the system to determine the at least one set of historical data relevant to the neurosurgical procedure by determining at least one set of historical data associated with tissue analysis data similar to tissue analysis data associated with the neurosurgical procedure, and to determine the at least one historical instance of the at least one procedure parameter by determining at least one tissue diagnosis associated with the at least one set of historical data.

18. The method of claim 14, wherein providing the central system comprises providing the planning module further causing the system to determine the at least one set of historical data relevant to the neurosurgical procedure by determining at least one set of historical data associated with image data similar to image data associated with the neurosurgical procedure.

19. The method of claim 14, wherein providing the central system comprises providing the planning module further causing the system to cause the output device to display at least one procedure outcome associated with the at least one set of historical data.

20. The method of claim 14,
wherein providing the central system comprises providing the planning module further causing the system to: access at least one of: at least one other local database and a remote database; determine additional data characterizing the neurosurgical procedure, the additional data being determined to be relevant to the neurosurgical procedure based on identification information included in a first set of data; and include the additional data into the first set of data,
wherein providing the central system comprises providing the planning module further causing the system to determine the at least one set of historical data relevant to the neurosurgical procedure by determining at least one set of historical data associated with tissue analysis data similar to tissue analysis data associated with the neurosurgical procedure, and to determine the at least one historical instance of the at least one procedure parameter by determining at least one tissue diagnosis associated with the at least one set of historical data,
wherein, providing the central system, the first set of data comprises image data associated with the neurosurgical procedure, providing the central system comprising providing the planning module further causing the system to receive input selecting a location in the image data, and determine the at least one set of historical data relevant to the neurosurgical procedure based on tissue analysis data associated with the selected location,
wherein providing the central system comprises providing the planning module further causing the system to determine the at least one set of historical data relevant to the neurosurgical procedure by determining at least one set of historical data associated with image data similar to image data associated with the neurosurgical procedure, and
wherein providing the central system comprises providing the planning module further causing the system to cause the output device to display at least one procedure outcome associated with the at least one set of historical data.

* * * * *